US010894832B2

(12) United States Patent
Ravetch et al.

(10) Patent No.: US 10,894,832 B2
(45) Date of Patent: *Jan. 19, 2021

(54) ANTI-INFLAMMATORY POLYPEPTIDES

(71) Applicant: The Rockefeller University, New York, NY (US)

(72) Inventors: Jeffrey V. Ravetch, New York, NY (US); Andrew Pincetic, New York, NY (US)

(73) Assignee: The Rockefeller University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/845,487

(22) Filed: Dec. 18, 2017

(65) Prior Publication Data

US 2018/0179284 A1     Jun. 28, 2018

Related U.S. Application Data

(63) Continuation of application No. 14/638,905, filed on Mar. 4, 2015, now Pat. No. 9,845,358, which is a continuation-in-part of application No. 14/368,701, filed as application No. PCT/US2012/068718 on Dec. 10, 2012, now Pat. No. 9,587,025.

(60) Provisional application No. 61/577,361, filed on Dec. 19, 2011.

(51) Int. Cl.
*C07K 16/28*     (2006.01)
*A61K 39/00*     (2006.01)

(52) U.S. Cl.
CPC .... *C07K 16/2851* (2013.01); *A61K 2039/505* (2013.01); *C07K 2317/41* (2013.01); *C07K 2317/52* (2013.01); *C07K 2317/70* (2013.01); *C07K 2317/72* (2013.01); *C07K 2318/00* (2013.01)

(58) Field of Classification Search
None
See application file for complete search history.

(56) References Cited

U.S. PATENT DOCUMENTS

| 7,846,744 | B2 | 12/2010 | Ravetch et al. |
| 8,188,231 | B2 | 5/2012 | Lazar et al. |
| 8,465,741 | B2 | 6/2013 | Frey |
| 2002/0164328 | A1 | 11/2002 | Shinkawa et al. |
| 2004/0110930 | A1 | 6/2004 | Reinl et al. |
| 2005/0207977 | A1 | 9/2005 | Reinl et al. |
| 2006/0153838 | A1 | 7/2006 | Watkins et al. |
| 2010/0172911 | A1 | 7/2010 | Naso et al. |

(Continued)

FOREIGN PATENT DOCUMENTS

| EA | 200870411 A1 | 4/2009 |
| EP | 2815768 A2 | 12/2014 |

(Continued)

OTHER PUBLICATIONS

Anthony et al., "Identification of a receptor required for the anti-inflammatory activity of IVIG," PNAS vol. 105, No. 50: 19571-19578 (Year: 2008).*

(Continued)

*Primary Examiner* — M Franco G Salvoza
(74) *Attorney, Agent, or Firm* — Fox Rothschild LLP

(57) ABSTRACT

This invention concerns anti-inflammatory agents, compositions, and methods for treating inflammatory disorders.

5 Claims, 10 Drawing Sheets
Specification includes a Sequence Listing.

a

Asialo-Fc—ChainA

Sial-Fc—ChainA b

(56) References Cited

U.S. PATENT DOCUMENTS

| | | | |
|---|---|---|---|
| 2010/0278808 A1* | 11/2010 | Ravetch | C07K 16/06 424/130.1 |
| 2010/0286067 A1 | 11/2010 | DeFrees | |
| 2012/0258041 A1 | 10/2012 | Basi | |
| 2014/0112914 A1 | 4/2014 | Nezu | |
| 2014/0377280 A1 | 12/2014 | Ravetch et al. | |

FOREIGN PATENT DOCUMENTS

| | | | | |
|---|---|---|---|---|
| JP | 2008539753 A | 11/2008 | | |
| NZ | 597651 A | 7/2012 | | |
| WO | WO-2006076594 A2 * | 7/2006 | | C07K 16/00 |
| WO | 2007/005786 A2 | 1/2007 | | |
| WO | 2007039818 A2 | 4/2007 | | |
| WO | 2007055916 A2 | 5/2007 | | |
| WO | 2007117505 A2 | 10/2007 | | |
| WO | 2008076487 A2 | 6/2008 | | |
| WO | 2008147143 A2 | 12/2008 | | |
| WO | 2011059684 A1 | 5/2011 | | |
| WO | 2013/095966 A1 | 6/2013 | | |

OTHER PUBLICATIONS

Rudikoff et al., "Single amino acid substitution altering antigen-binding specificity," Proc Natl Acad Sci USA 79:1979-1983 (Year: 1982).*

Kaneko et al., "Anti-Inflammatory Activity of Immunoglobulin G Resulting from Fc Sialylation," Science, vol. 313: 670-673 (Year: 2006).*

NCBI Blast Comparison of SEQ ID No. 1 of U.S. Pat. No. 9845358 and Instant SEQ ID No. 2 (Year: 2019).*

Ahmed et al., "Structural Characterization of Anti-Inflammatory Immunoglobulin G Fc Proteins," Journal of Molecular Biology (Sep. 1, 2014): 426(18):3166-3179.

Anthony et al., "A Novel Role for the IgF Fc Glycan: The Anti-inflammatory Activity of Sialylated IgG Fcs," J Clin Immunol 30 (Suppl 1): S9-S14 (2010).

Anthony et al., "Identification of a receptor required for the anti-inflammatory activity of IVIG," PNAS vol. 105, No. 50: 19571-19578 (2008).

Anthony et al., "Recapitulation of IVIG anti-inflammatory activity with a recombinant IgG Fc," Science (Apr. 18, 2008): 320(5874):373-376.

Blomberg, "Intrathecal and Systemic Complement Activation Studies of Multiple Sclerosis and Guillan-Barre Syndrome," Biomedicine 240 hp, University of Kalmar, Examination Project Work (2009).

Burton et al. "Sugar Determnies Antibody Activity," Science (Aug. 4, 2006):313:627-628.

Campell et al., Therapeutic Effect of IV1G on Inflammatory Arthritis in Mice is Dependent on the Fc Portion and Independent of Sialylation or Basophils, the Journal of Immunology (Apr. 23, 2014); 192(11):5031-5038.

Fiebiger et al., "Protection in antibody- and T cell-mediated autoimmune diseases by antiinflammatory igG Fcs requires type II FcRs," PNAS (Published online Apr. 13, 2015), pp. E2385-E2394.

Ha et al., "Isolation and characterization of IgG1 with asymmetrical Fc glycosylation," Glycobiology (2011); 21(8):1087-1096.

Igawa et al., "Engineering the variable region of therapeutic IgG antibodies," mAbs 3:3: 243-252 (2011).

Jassal et al., "Sialylation of Human IfG-Fc Carbohydrate by Transfected Rat a2,6-Sialyltransferase," Biochemical and Biophysical Research Communications (2001); 286:243-249.

Kaneko et al., "Anti-inflammatory Activity of Immunoglobulin G Resulting from Fc Sialylation," Science, vol. 313:670 (2006).

Kessel et al., "Intravenous Immunoglobulin Therapy Affects T Regulatory Cells by Increasing Their Suppressive Function," The Journal of Immunology (2007) 179:5571-5575.

Lefevre et al., "Alanine-stretch scanning mutagenesis: a simple and efficient method to probe protein structure and function," Nucleic Acids Research, vol. 25, No. 2: 447-448 (1997).

Lund et al., "Multiple Interactions of IgG with its Core Oligosaccharide Can Modulate Recognition by Complement and Human Fc gamma Receptor I and influence the Synthesis of its Oligosaccharide Chains." The Journal of Immunology (Dec. 1, 1996);157(11):4963-4969.

Nimmerjahn et al., "Anti-Inflammatory Actions of Intravenous Immunoglobulin," Annu. Rev. Immunol. (2008); 26:513-533.

Palladino et al., "Anti-TNF-a Therapies: The Next Generation," Nature (Sep. 2003); 2(9):736-746.

Pavlovic et al., "Intravenous immunoglobulins exposed to heme (heme IVIG) are more effiient than IVIG in attenuating autoimmune diabetes," Clinical Immunology (2011); 138:162-171.

Ramakrishna et al., "Passively Administered Pooled Human Immunoglobulins Exert IL-10 Dependent Anti-Inflammatory Effects That Protect Against Fatal HSV Encephalitis," PLoS Pathog. (Jun. 2, 2011):7(6):1-17.

Rudikoff et al. ("Single amino acid substitution altering antigen-binding specificity," Proc Natl Acad Sci USA 79:1979-1983 (1982).

Scallon et al., "Higher levels of sialyated Fc glycans in immunoglobulin G molecules can adversely impact functionality," Molecular Immunology (2007); 44:1524-1534.

Stadlmann et al., "A Close Look at Human IgG Sialylation and Subclass Distribution After Lectin Fractionation," Proteomics. (Sep. 1, 2009); 9(17):4143-4153.

Stadlmann et al., Analytical and Functional Aspects of Antibody Sialylation, Journal of Clinical Immunology (May 1, 2010); 30(Supp. 1):S15-S19.

Yu et al., "Engineering Hydrophobic Protein-Carbohydrate Interactions to Fine-Tune Monoclonal Antibodies," Journal of the American Chemical Society, (Jul. 3, 2013); 135(26):9723-9732.

Weikert et al., "Engineering Chinese hamster ovary cells to maximize sialic acid content of recombinant glycoproteins," Nature Biotechnology (Nov. 1999); 17:1116-1121.

Ephrem et al., "Expansion of CD4+CD25+ regulatory T cells by intravenous immunoglobulin: a critical factor in controlling experimental autoimmune encephalomyelitis," Blood (2007); 111: 715-722.

Trinath et al., "Intravenous immunoglobulin expands regulatory T cells via induction of cyclooxygenase-2-dependent prostaglandin E2 in human dendritic cells," Blood (2013); 122(8): 1419-1427.

Anthony et al., "A Recombinant IgF Fc That Recapitulates the Anti-Inflammatory Activity of IVIG," Science 320(5874): 373-376 (2008).

Katz et al., "Long Term Safety of IVIg Theraphy in Multiple Sclerosis: 10 Years Experience," Autoimmunity 39(6): 513-517 (2006).

Pöhlau et al., "Intravenous Immunoglobulin in Primary and Secondary Chronic Progressive Multiple Sclerosis: A Randomized Placebo Controlled Multicentre Study," Multiple Sclerosis 13: 1107-1117 (2007).

Smith et al., "Fc?RIIB in autoimmunity and infection: evolutionary and therapeutic implications", Nat Rev Immunol., 2010, 10(5): 328-343.

* cited by examiner

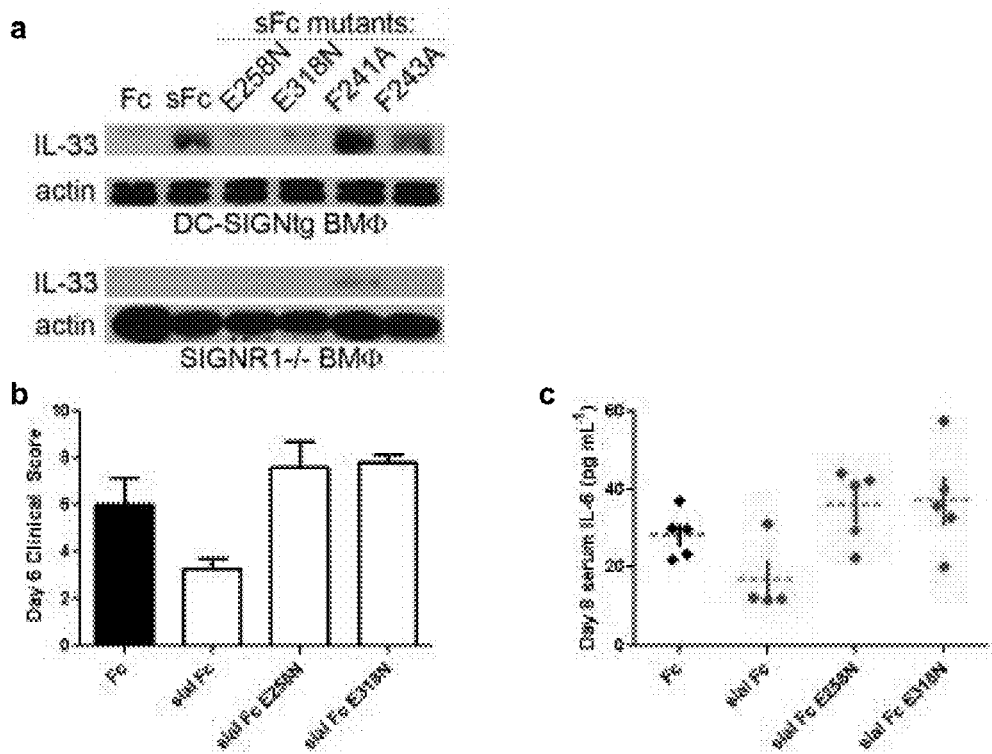
FIGs. 9A, 9B and 9C
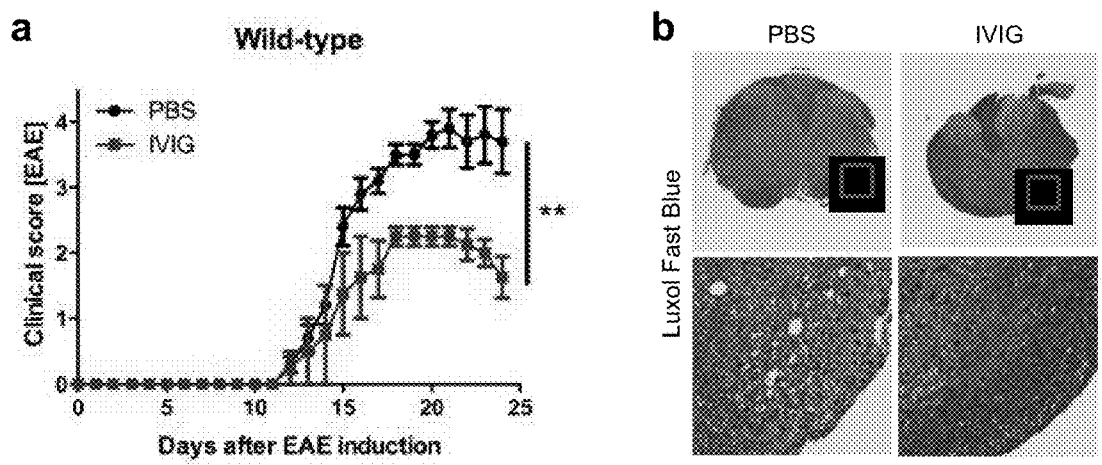
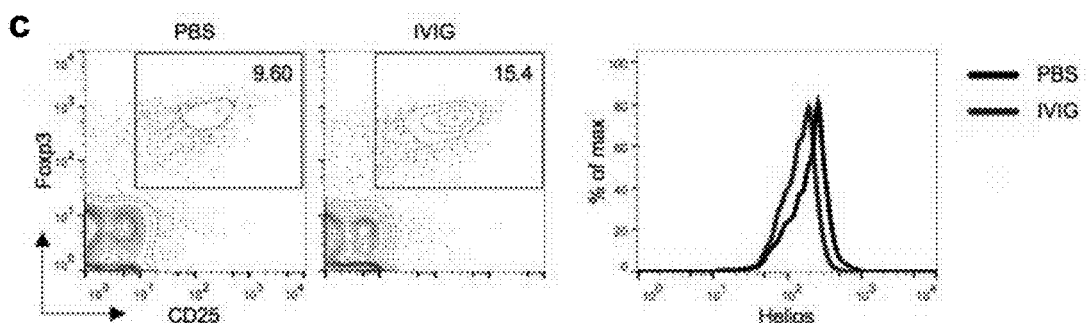
FIGs. 10A, 10B and 10C

SEQUENCE LISTING

<160> NUMBER OF SEQ ID NOS: 8

<210> SEQ ID NO 1
<211> LENGTH: 238
<212> TYPE: PRT
<213> ORGANISM: Homo sapiens

<400> SEQUENCE: 1

Lys Val Asp Lys Arg Val Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 2

<211> LENGTH: 238
<212> TYPE: PRT
<213> ORGANISM: Artificial
<220> FEATURE:
<223> OTHER INFORMATION: Synthetic

<400> SEQUENCE: 2

Lys Val Asp Lys Arg Val Glu Pro Lys Ser Cys Asp Lys Thr His Thr
1               5                   10                  15

Cys Pro Pro Cys Pro Ala Pro Glu Leu Leu Gly Gly Pro Ser Val Ala
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
210                 215                 220

Asn His Tyr Thr Gln Lys Ser Leu Ser Leu Ser Pro Gly Lys
225                 230                 235

<210> SEQ ID NO 3
<211> LENGTH: 238
<212> TYPE: PRT
<213> ORGANISM: Artificial
<220> FEATURE:
<223> OTHER INFORMATION: Synthetic

<400> SEQUENCE: 3

Lys Val Asp Lys Arg Val Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Ala Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val

```
                85                  90                  95
Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
tcactgcagg aaagtacagc a                                              21

<210> SEQ ID NO 5
<211> LENGTH: 20
<212> TYPE: DNA
<213> ORGANISM: Artificial
<220> FEATURE:
<223> OTHER INFORMATION: Synthetic

<400> SEQUENCE: 5
agtagcacct ggtcttgctc                                                20

<210> SEQ ID NO 6
<211> LENGTH: 21
<212> TYPE: DNA
<213> ORGANISM: Artificial
<220> FEATURE:
<223> OTHER INFORMATION: Synthetic

<400> SEQUENCE: 6
acagtccatg ccatcactgc c                                              21

<210> SEQ ID NO 7
<211> LENGTH: 21
<212> TYPE: DNA
<213> ORGANISM: Artificial
<220> FEATURE:
<223> OTHER INFORMATION: Synthetic

<400> SEQUENCE: 7
gcctgcttca ccaccttctt g                                              21

<210> SEQ ID NO 8
```

```
<211> LENGTH: 21
<212> TYPE: PRT
<213> ORGANISM: Artificial
<220> FEATURE:
<223> OTHER INFORMATION: Synthetic

<400> SEQUENCE: 8

Met Glu Val Gly Trp Tyr Arg Ser Pro Phe Ser Arg Val Val His Leu
1               5                   10                  15

Tyr Arg Asn Gly Lys
            20
```

ANTI-INFLAMMATORY POLYPEPTIDES

CROSS REFERENCE TO RELATED APPLICATIONS

This application is a Continuation of U.S. application Ser. No. 14/638,905, filed Mar. 4, 2015, which is a Continuation-In-Part application of U.S. application Ser. No. 14/368,701, filed on Jun. 25, 2014, now U.S. Pat. No. 9,587,025, which is a U.S. National Phase based on International Application No. PCT/US2012/068718, filed on Dec. 10, 2012, which claims priority to U.S. Provisional Application No. 61/577,361, filed on Dec. 19, 2011. The contents of which are all incorporated herein by reference in their entireties.

FIELD OF INVENTION

This invention relates to anti-inflammatory agents, compositions, and methods for treating inflammatory disorders.

BACKGROUND

Inflammatory disorders, including autoimmune diseases, are disorders involving abnormal activation and subsequent migration of white blood cells to affected areas of the body. These conditions encompass a wide range of ailments that affect the lives of millions of people throughout the world. Although various treatments are presently available, many possess significantly side effects or are not very effective in alleviating all symptoms. Thus, there are needs for anti-inflammatory agents for treating inflammatory disorders and needs for methods of identifying and evaluating such agents.

Immunoglobulin G (IgG) has long been appreciated to mediate both pro- and anti-inflammatory activities through interactions mediated by its Fc fragment. While Fc-FcγR interactions are responsible for the pro-inflammatory properties of immune complexes and cytotoxic antibodies, intravenous gamma globulin (IVIG) and its Fc fragments are anti-inflammatory and are widely used to suppress inflammatory diseases. It has been proposed that glycosylation of IgG is crucial for regulation of cytotoxicity and inflammatory potential of IgG. For example, it has been suggested that anti-inflammatory activity of IVIG is a property of the Fc fragment and its linked glycan, requiring terminal $\alpha.2,6$ sialic acid linkages, indicating a combined requirement for the specific polypeptide backbone and glycan structure for immunosuppression. (Anthony, et al., 2008, Science 320: 373-376 and WO 2007/117505).

However, only a minor population of IgG in IVIG have glycans terminating in $\alpha 2,6$ sialic acids (sFc) and the anti-inflammatory activity. As a result, for the suppression of autoantibody triggered inflammation in a variety of clinical settings, one has to administer IVIG at high doses (1-2 g/kg), to enrich sialylated IgGs, or otherwise to increase the sialylation of IgGs (U.S. Application Nos. 20080206246, and 20090004179, and Nimmerjahn et al. *Annu Rev Immunol* 26, 513-533 (2008)).

The present invention addresses and meets the above-mentioned needs by identifying sialylation-free anti-inflammatory polypeptides.

SUMMARY

This invention relates to agents, such as polypeptides and antibodies, and methods for treating inflammatory disorders, e.g., autoimmune diseases.

Accordingly, one aspect of this invention features an isolated polypeptide comprising a modified sequence that is at least 75% (e.g., any number between 75% and 100%, inclusive, e.g., 75%, 80%, 85%, 90%, 95%, 99%, and 100%) identical to an IgG Fc region. The modified sequence is free of sialylation and the polypeptide has an anti-inflammatory activity that is higher than that of a parent polypeptide. The parent polypeptide can comprise the IgG Fc region, such as the sequence of SEQ ID NO: 1 listed below. In some embodiments, the polypeptide has ability to bind to DC-SIGN, and to bind to hFcγRIIA or RIIB In one embodiment, the isolated polypeptide has an ability to bind to hFcγRIIA or RIIB at a $K_D$ of $2\times10^{-5}$ M or lower (i.e., $K_A$ of $5.0\times10^4$ $M^{-1}$ or higher). Preferably, the modified sequence has a FA241 mutation. The modified sequence can be at least 75% (e.g., any number between 75% and 100%, inclusive, e.g., 75%, 80%, 85%, 90%, 95%, 99%, and 100%) identical to SEQ ID NO: 2. In some examples, the modified sequence comprises or consists essentially of SEQ ID NO: 2.

In another aspect, the invention provides a method for making a polypeptide having an anti-inflammatory activity. The method includes, among others, steps of providing a parent polypeptide having the sequence of an IgG Fc region or a first nucleic acid sequence encoding the parent polypeptide; and modifying the parent polypeptide to obtain a modified polypeptide so that the modified polypeptide is free of sialylation and mimics the structural of a sialylated form of the IgG Fc region. The modifying step can be conducted by modifying the first nucleic acid sequence to obtain a second nucleic acid encoding the modified polypeptide. The invention also provides a polypeptide made by the just-described method.

In a third aspect, the invention features an isolated nucleic acid comprising a sequence encoding the polypeptide described above; an expression vector comprising the nucleic acid; and a host cell comprising the nucleic acid. The invention also features a method of producing a polypeptide. The method includes culturing the host cell in a medium under conditions permitting expression of a polypeptide encoded by the nucleic acid, and purifying the polypeptide from the cultured cell or the medium of the cell.

In a fourth aspect, the invention features a pharmaceutical formulation comprising (i) the polypeptide or nucleic acid described above, and (ii) a pharmaceutically acceptable carrier.

In a fifth aspect, the invention provides a method of treating an inflammatory disease. The method includes administering to a subject in need thereof a therapeutically effective amount of the above-described polypeptide or nucleic acid encoding the polypeptide. Also provided is use of the polypeptide or nucleic acid in the manufacture of a medicament for treating an inflammatory disease. The invention also features an isolated polypeptide, nucleic acid, expression vector, host cell, composition, or method for treating an inflammatory disease substantially as shown and described herein.

In another aspect, the invention further provides a method of increasing a level of regulatory T ($T_{reg}$) cells in a subject in need thereof. The method comprises administering to the subject an effective amount of (i) a first isolated polypeptide comprising an IgG Fc region that is sialylated; or (ii) a second isolated polypeptide comprising a modified sequence that is at least 75% (e.g., any number between 75% and 100%, inclusive, e.g., 75%, 80%, 85%, 90%, 95%, 99%, and 100%) identical to the IgG Fc region or a nucleic acid encoding the second polypeptide, wherein the modified sequence has a FA241 mutation. In one embodiment, the subject has an inflammatory disease, such as an autoimmune disease, including a T cell-mediated autoimmune disease. Examples of the T cell-mediated autoimmune disease include multiple sclerosis and type I diabetes. Accordingly, the invention also provides a method treating a T cell-mediated autoimmune disease in a subject in need thereof. The method comprises administering to the subject an effective amount of the above-mentioned first isolated polypeptide or second isolated polypeptide or nucleic acid.

In preferred embodiments, the IgG region in the first isolated polypeptide can be sialylated at a level higher than that of IgG in the subject. The modified sequence can be sialylated at different levels or non-sialylated. In some embodiments, it is (a) substantially free of sialylation or (b) sialylated at a level lower than that of IgG of the subject. The IgG Fc region can comprise the sequence of SEQ ID NO: 1. The modified sequence can be at least 75% (e.g., any number between 75% and 100%, inclusive, e.g., 75%, 80%, 85%, 90%, 95%, 99%, and 100%) identical to SEQ ID NO: 2. The first or second isolated polypeptide has an ability to bind to DC-SIGN, hFcγRIIA, or hFcγRIIB Preferably, the isolated polypeptide has an ability to bind to hFcγRIIA or hFcγRIIB at a $K_D$ of $2\times10^{-5}$ M or lower (i.e., $K_A$ of $5.0\times10^4$ $M^{-1}$ or higher).

The details of one or more embodiments of the invention are set forth in the description below. Other features, objects, and advantages of the invention will be apparent from the description and from the claims.

DESCRIPTION OF DRAWINGS

FIGS. 9A, 9B and 9C show that the E318/Lys340 pocket is critical for the anti-inflammatory effect of sialylated Fc. (a) Bone marrow cells from SIGN-R1$^{-/-}$ and hDC-SIGN$^+$ mice were isolated and differentiated in vitro into macrophages (BMMΦ). BMMΦ were pulsed with wild-type or mutant Fc overnight. Whole cell extracts were used for western blotting. Actin served as loading control. (b) K/BxN-challenged C57BL/6 mice were treated with different Fc preparations. Clinical scores of disease were monitored on day six post treatment. (c) Serum IL-6 levels were tested by ELISA 8 days post treatment.

FIGS. 10A, 10B and 10C: IVIG selectively expands inducible T_{reg} cells. EAE was induced in C57BL/6 wild-type mice by immunization with MOG_{35-55} peptide emulsified in CFA. Mice were treated with PBS or IVIG (1 g/kg). (a) Clinical scores of EAE are depicted. Means+/−SEM are plotted: **p<0.01 determined by Tukey's post-hoc test. (b) Representative images of HE and Luxol Fast Blue staining of spinal cords from EAE mice. HE staining for inflammation. Loss of signal in the Luxol Fast Blue staining reflects progressed demyelination. (c) Cells from draining lymph nodes were isolated and analyzed for T_{reg} cell numbers and their expression of the nT_{reg}-specific transcription factor Helios.

DETAILED DESCRIPTION

Figures 1A, 1B, 1C, 1D:
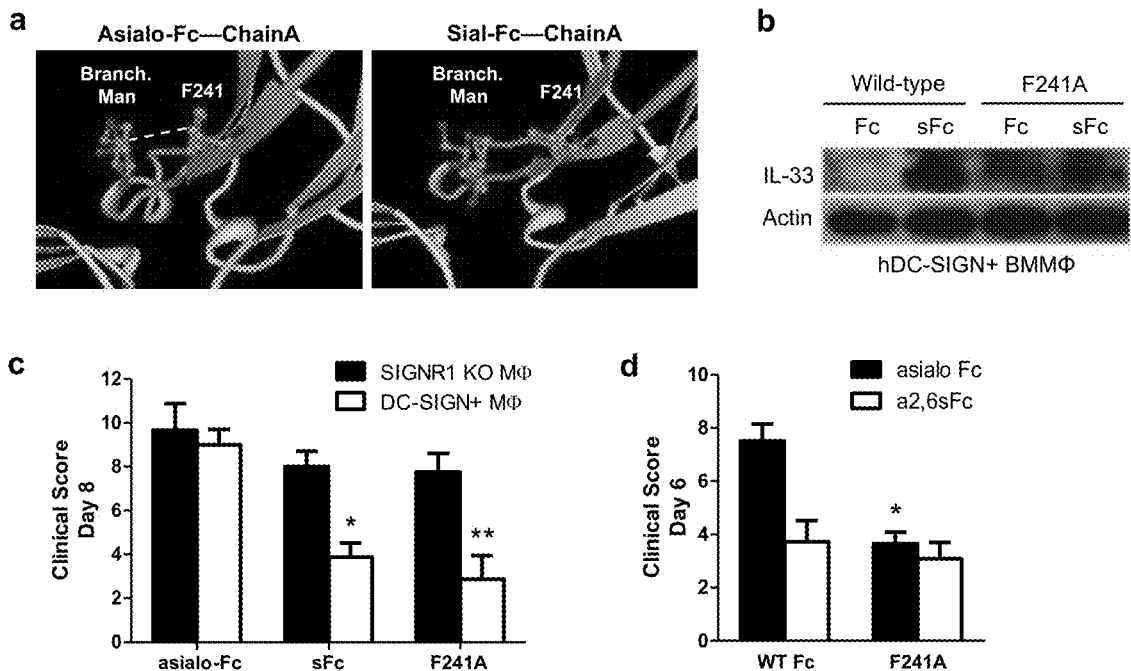
FIGS. 1A, 1B, 1C and 1D show that F241A is capable of suppressing serum-induced arthritis. (a) Schematic depiction of the interaction between mannose residues of the non-sialylated core glycan (Asialo-Fc) with the phenylalanine residue at position 241 of the Cγ2 domain. Upon sialylation (Sial-Fc) this interaction no longer occurs, resulting in a higher conformational flexibility of the Fc portion to switch between the so-called open and closed conformation. (b) hDC-SIGN$^+$ bone marrow-derived macrophages were pulsed for 1 hour with sialylated (sFc) or non-sialylated (Fc) wild-type Fc or F241A-Fc. Whole cell extracts were used to analyze IL-33 production by western blotting. Actin served as loading control. (c) BMMΦ from either SIGN-R1$^{-/-}$ or hDC-SIGN$^+$ mice were pulsed with non-sialylated wild-type Fc (asialo-Fc), sialylated wild-type Fc (sFc) or F241A. After extensive washes the cells were adoptively transferred into K/BxN challenged C57BL/6 mice. (d) hDC-SIGN$^+$ BMMΦ were pulsed with either asialylated (asialo Fc) or sialylated (α2,6sFc) variants of wild-type Fc or F241A. The cells were adoptively transferred into K/BxN challenged C57BL/6 mice. Means+/−SEM are plotted; *p<0.05; **p<0.01 determined by Tukey's post-hoc test.

This invention is based, at least in part, on unexpected discoveries that non-sialylated IgG Fc variants confer anti-inflammatory activity and mimic the effect of 2,6 sialylated Fc as anti-inflammatory mediators and that structural alterations induced by sialylation can be mimicked by specific amino acid modifications to the C_H2 domain. It was also unexpected that both the variants and sialylated Fc activates T_{reg} cells.

As disclosed herein, the anti-inflammatory activity of IVIG is dependent on the presence of sialic acid in the core IgG-Fc glycan, resulting in increased conformational flexibility of the C_H2 domain, with corresponding modulation of FcR binding specificity from type I to type II receptors. Sialylated IgG-Fc (sFc) increases the activation threshold of innate effector cells to immune complexes by stimulating the up-regulation of the inhibitory receptor FcγRIIB The inventors have found that the structural alterations induced by sialylation can be mimicked by specific amino acid modifications to the C_H2 domain. For example, an IgG-Fc variant with a point mutation at position 241 (F-A) exhibits anti-inflammatory activity even in the absence of sialylation. F241A and sFc protect mice from arthritis in both collagen and KBxN-induced models and, in the T cell-mediated EAE mouse model, suppressed disease by specifically activating $T_{reg}$ cells. Protection by these anti-inflammatory Fcs in both antibody- and T cell-mediated autoimmune diseases required type II FcRs and the induction of IL-33. These results further clarify the mechanism of action of IVIG in both antibody and T cell-mediated inflammatory diseases and demonstrate that Fc variants that mimic the structural alterations induced by sialylation, such as F241A, can be used for the treatment of various autoimmune disorders.

IgG and Fc Sialylation

IgG is the major serum immunoglobulin. It is a glycoprotein composed of two identical heavy chains and two light chains, which in turn are composed of variable and constant domain. IgG contains a single, N-linked glycan at $Asn^{297}$ in the CH2 domain on each of its two heavy chains. The covalently-linked, complex carbohydrate is composed of a core, biantennary penta-polysaccharide containing N-acetylglucosamine (GlcNAc) and mannose (man). Further modification of the core carbohydrate structure is observed in serum antibodies with the presence of fucose, branching GlcNAc, galactose (gal) and terminal sialic acid (sa) moieties variably found. Over 40 different glycoforms have thus been detected to be covalently attached to this single glycosylation site (Fujii et al., J. Biol. Chem. 265, 6009, 1990). Glycosylation of IgG has been shown to be essential for binding to all FcγRs by maintaining an open conformation of the two heavy chains. Jefferis and Lund, Immune. Lett. 82, 57 (2002), Sondermann et al., J. Mol. Biol. 309, 737 (2001). It is believed that this IgG glycosylation for FcγR binding accounts for the inability of deglycosylated IgG antibodies to mediate in vivo triggered inflammatory responses, such as ADCC, phagocytosis and the release of inflammatory mediators. Nimmerjahn and Ravetch, Immunity 24, 19 (2006). Further observations that individual glycoforms of IgG may contribute to modulating inflammatory responses has been suggested by the altered affinities for individual FcγRs reported for IgG antibodies containing or lacking fucose and their consequential affects on cytotoxicity. Shields et al., J. Biol. Chem. 277, 26733 (2002), Nimmerjahn and Ravetch, Science 310, 1510 (2005). A link between autoimmune states and specific glycosylation patterns of IgG antibodies has been observed in patients with rheumatoid arthritis and several autoimmune vasculities in which decreased galactosylation and sialylation of IgG antibodies have been reported. Parekh et al., Nature 316, 452 (1985), Rademacher et al., Proc. Natl. Acad. Sci. USA 91, 6123 (1994), Matsumoto et al., 128, 621 (2000), Holland et al., Biochim. Biophys. Acta December 27. Variations in IgG glycoforms have also been reported to be associated with aging and upon immunization, although the in vivo significance of these alterations has not been determined. Shikata et al., Glycoconj. J. 15, 683 (1998), Lastra, et al., Autoimmunity 28, 25 (1998).

IgG Fc Variants

As disclosed herein, certain IgG Fc variants, sialylated or not, surprisingly also confer anti-inflammatory activity. Such variants, including the FA241 variant, represent species within a larger genus of molecules that, by virtue of mimicking the structural and biological properties of sialylated Fc, but do not require sialylation, can be developed as anti-inflammatory therapeutics.

IVIG, although initially developed as an immunoglobulin replacement therapy in patients with hypogammagloubilinenemia, has gained widespread use for its immunomodulatory activities. It is an approved therapeutic for the treatment of autoimmune disorders such as immunothrombocytopenia (ITP), chronic inflammatory demyelinating polyneuropathy (CIDP), Kawasaki's disease, and Guillain-Barre syndrome, and is used in a growing number of autoimmune and inflammatory disorders. Its anti-inflammatory activity has been shown to result from the presence of a specific glycan, the α2,6-sialylated, complex bi-antennary structure present on the $C_H2$ domain of the Fc, and found in small proportion of the heterogenous antibody preparations in IVIG. Sialylation of the Fc glycan on the $C_H2$ domain results in IgGs that can engage type II Fc receptors such as SIGN-R1, DC-SIGN, and CD23, while reducing their binding affinity to type I FcRs. Studies in mouse models of serum induced arthritis, antibody-dependent ITP, nephrotoxic nephritis, and autoimmune blistering diseases (ABD) confirmed the anti-inflammatory activity of the sialylated Fc, whether from IVIG or generated from recombinantly expressed IgG1. Moreover, increasing the percentage of sialylated Fc fragments either in IVIG or recombinant expressed IgG1 resulted in an enhanced therapeutic potency of these preparations. Elucidation of the mechanism by which sFc induces an anti-inflammatory response was first reported in murine models of arthritis, demonstrating that selective binding of sialylated Fc to type II FcRs resulted in the production of IL-33 by regulatory macrophages, that in turn stimulated IL-4 secretion from basophils. IL-4 induced the up-regulation of the inhibitory receptor FcγRIIB on effector macrophages thereby increasing the activation threshold of these cells and suppressing inflammation. Subsequent studies have confirmed that IVIG treatment of human populations resulted in both increased serum IL-33 levels and FcγRIIB expression on lymphoid and myeloid cells, consistent with the murine data.

As disclosed herein crystallographic and biophysical studies on sialylated and asialylated IgG Fc fragments have provided insights into the structural basis for the anti-inflammatory activity of sialylated Fc. Sialylation of the complex, bi-antennary glycan of the IgG Fc results in increased conformational flexibility of the $C_H2$ domain, thereby sampling the closed conformations of the $C_H2$ domain required for type II FcR binding. In contrast, asialylated Fc structures uniformly result in open Fc conformations, consistent with their binding specificity for type I FcRs. Glycan interactions with amino acid residues of the $C_H2$ domain are disrupted upon sialylation, providing a basis for the observed conformational changes seen in the protein structure and consistent with a model proposed for the binding specificity of sialylated Fc for type II FcRs. Based on these observations the inventors generated a series of Fc variants, targeting the amino acids of the $C_H2$ domain that interact with the glycan, with the goal of determining their impact on type II FcR binding and the resulting anti-inflammatory activity. Both gain and loss of function mutants were examined in this study. The identification of a gain of function variant, which could mimic the conformational state induced by sialylation, without requiring this specific carbohydrate modification, can simplify the development of anti-inflammatory IgG Fc for therapeutic use. The inventors succeeded in identifying a mutation (F241A) predicted to increase mobility of the α1,3-arm, and which replicates the anti-inflammatory activity of sialylated Fc even in the absence of sialylation. The inventors have characterized this variant, in comparison to sialylated Fc, in both antibody and T cell models of autoimmune inflammation.

While the basis for IVIG protection in antibody-mediated models of inflammation have been extensively studied, as summarized above, recent studies have demonstrated that IVIG can also protect in classical T cell-mediated autoimmune disorders, such as EAE as well as in a model of airway hyperresponsiveness (AHR). This therapeutic effect of IVIG is proposed to result from the activation and expansion of $T_{reg}$ cells thus suppressing T cell responses by IFN γ-secreting $T_H1$ and IL-17-secreting $T_H17$ cells. The inventors therefore sought to investigate if the $T_{reg}$ cell activation and expansion was also the result of sialylated Fcs or the F241A variant. Using F241A, sialylated and asialylated IVIG, the inventors investigated the mechanisms of action of their immunomodulatory effects on $T_{reg}$ cell activation and suppression of T cell-dependent autoimmunity. The inventors demonstrate that the sialylation of IVIG is critically required for $T_{reg}$ cell activation and expansion and the F241A variant is sufficient to suppress T cell-dependent inflammation in the EAE and experimental colitis models. Furthermore, both sFc and F241A stimulate the production of Interleukin-33 (IL-33) that in turn activates $T_{reg}$ cells through the ST2 receptor contributing to the suppression of T cell-mediated autoimmune responses.

As disclosed in the examples below, the inventors present functional data demonstrating that specific interactions between the Fc backbone and the Fc glycan influence the effector properties of sialylated IgG. The inventors confirmed that the anti-inflammatory activity of sial Fc depends strictly on the α2,6-linkage of sialic acid since only α2,6-sial Fc, but not α2,3-sial Fc, binds to DC-SIGN and suppresses autoantibody-induced arthritic inflammation. How can different sialic acid linkages on the Fc glycan influence Fc structure? The inventors discovered that the proximity of the sialic acid sugar residue to the protein backbone may determine how sialic acid interacts with specific amino acid side chains on the Fc. Indeed, molecular modeling suggests that only α2,6-linked sialic acid could fit into a groove formed by Glu318 and Lys340 at the Cγ2-Cγ3 interface. To determine if this groove plays a role in the anti-inflammatory activity of α2,6-sial Fc, the inventors characterized the immunosuppressive functions of sial Fc bearing an E318N point mutation. Interestingly, the E318N α2,6-sial Fc fails to initiate anti-inflammatory pathways associated with WT α2,6-sial Fc, such as induction of IL-33 expression or protection from arthritic inflammation by adoptive transfer of stimulated DC-SIGN⁺ BMMΦ to K/BxN serum-challenged mice. Thus, as with the α2,3-linkage of sialic acid, the inventors propose that the E318N mutation abolished the interaction between α2,6-linked sialic acid and the Fc backbone necessary for the Fc to adopt its 'closed', anti-inflammatory state.

Fc structures typically resolve the α1,3 arms of the Fc glycan within the internal cavity formed by the $C_H2$ domains. By occupying this cavity, the α1,3 arms stabilize the $C_H2$ domains at a distance apart in the 'open' conformation to facilitate binding to type I FcRs. In order for the proposed model to be correct, the sialylated α1,3 arms have to move out of this cavity towards the $C_H2$-$C_H3$ interface so that the terminal sialic acid may contact the E318/K340 groove. Thus, by repositioning the sialylated α1,3 arms to the $C_H2$-$C_H3$ interface, the $C_H2$ domains may draw closer together to fill the now unoccupied cavity and form the 'closed' conformation. Unlike the α1,6 arm of the Fc glycan, which forms multiple non-covalent interactions with the Fc backbone, the α1,3 arm forms only one known contact in the absence of sialylation—the aromatic side chain of F241. However, in the crystal structure of sial Fc, the only amino acid side chain that contacts the Fc glycan to show a significant change in orientation is the ring structure of F241. The inventors believe that the observed 90° rotation of F241 abrogates the hydrophobic stacking interaction it normally forms with the carbohydrate. The inventors believe this to be structurally important because the disruption of this stabilizing interaction should impart greater degrees of freedom, or mobility, to the sialylated α1,3 arms of the Fc glycan. With this greater mobility, the sialylated α1,3 arms will sample the space outside of the internal cavity with greater frequency to encounter the E318/K340 pocket at the $C_H2$-$C_H3$ interface. Consistent with the crucial role of F241 in the structure of α2,6-sial Fc, the inventors found that an F241A mutation that specifically disrupts this protein-sugar contact point recapitulated the anti-inflammatory activity of sial Fc independent of sialylation. Both α2,6-sial and asial F241A Fc bound to DC-SIGN, induced IL-33 expression, and transferred anti-inflammatory activity with stimulated DC-SIGN⁺ BMMΦ to K/BxN serum-challenged mice, recapitulating the anti-inflammatory activity of IVIG and sialylated IgG. Recently, reports have been published that question the essential role of Fc sialylation for modulating immune responses. The data, and that of several other groups, have confirmed the anti-inflammatory role of sialylated Fc in multiple models of antibody-mediated inflammation. These discrepancies are likely the result of non-linear dosing of IVIG in selective models and thus not reflective of the physiologically relevant conditions in which IVIG is used.

Figure 15:
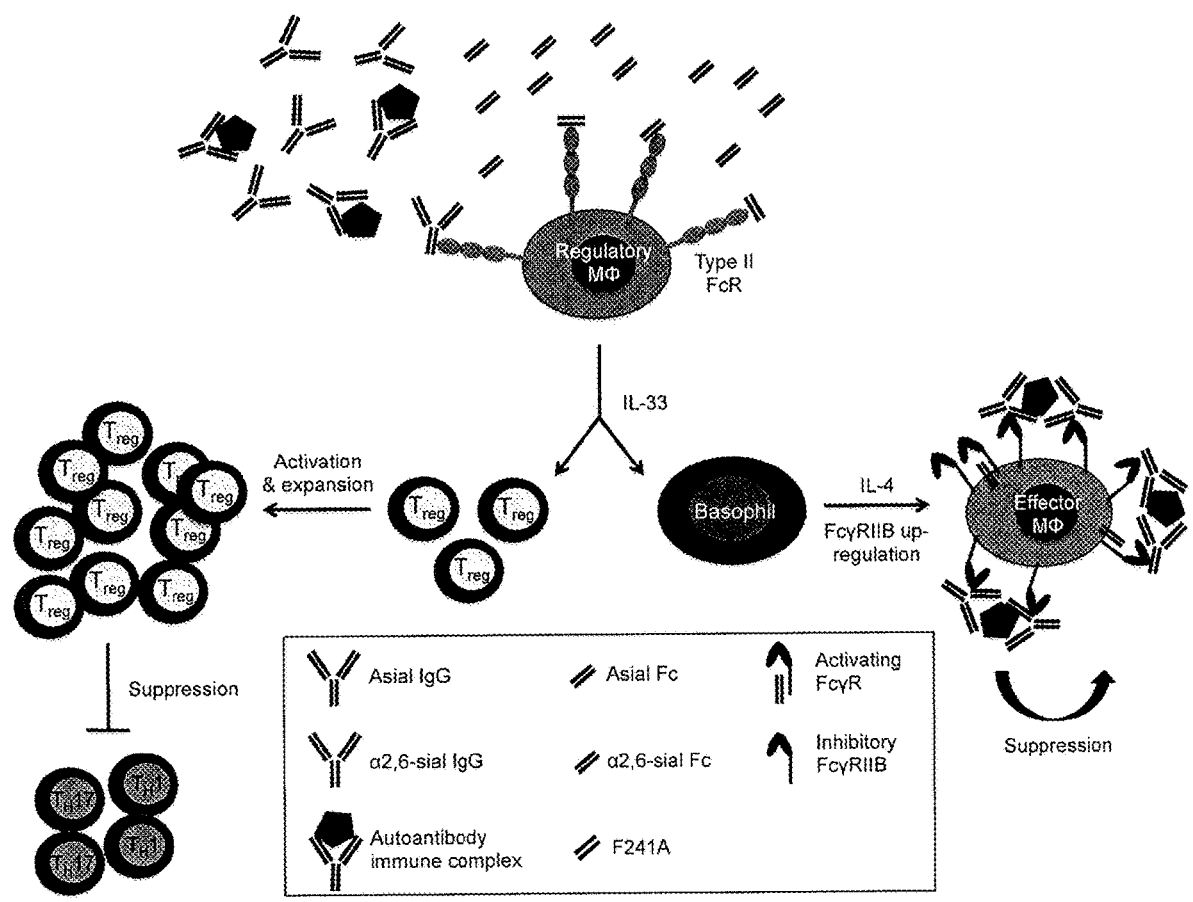
FIG. 15 shows a model of sFc-induced anti-inflammatory pathways: Sialylated IgG, sFc as well as the sialylated Fc analogue F241A selectively engage type II FcRs like SIGN-R1 or human DC-SIGN on regulatory macrophages and induce IL-33 production. IL-33 is a central mediator that induces two different anti-inflammatory pathways. Basophils respond to IL-33 with production of IL-4, which in turn induces the up-regulation of the inhibitory FcγRIIB on effector macrophages. The resulting dramatic change of their activation threshold suppresses inflammation. In addition, IL-33 also triggers activation and expansion of T_{reg} cells, which effectively suppress T_H1 and T_H17 cells, thus ameliorating T cell-mediated autoimmunity.

We have identified that sialylated Fc, as well as variants such as F241A, specifically stimulated $iT_{reg}$ cell expansion and were sufficient to suppress T cell-mediated immune responses in models of EAE and experimental colitis by selective engagement of the type II Fc receptors, SIGN-R1, or its human orthologue DC-SIGN. Furthermore, the inventors identified IL-33 as an essential mediator of this pathway. IL-33, induced in response to type II FcR engagement by IVIG, sialylated Fc, or F241A, acts pleiotropically, as summarized in FIG. 15. It can mediate IL-4 secretion by basophils to polarize macrophages to an M2 phenotype and induce inhibitory FcγRIIB expression, a pathway that dominates in antibody-mediated autoimmune inflammation, or it can act directly on $T_{reg}$ cells to mediate their activation and expansion. The inventors demonstrated that $T_{reg}$ cells can become activated by the therapeutic treatment with sialylated Fc that critically relies on the signaling through the IL-33/ST2 axis. The inventors cannot exclude the possibility that the IL-33-dependent $T_{reg}$ cell activation is mainly mediated indirectly via dendritic cells as previously described by Matta and coworkers. However, the inventors did not detect any direct interaction of IVIG with any T cell subset, neither effector nor $T_{reg}$ cells, in contrast to a recently proposed model, nor could the inventors observe any evidence in support of IVIG providing "Tregitopes". Specifically, the inventors could detect $T_{reg}$ cell activation and expansion in experiments in which IVIG- or F241A-treated hDC-SIGN⁺ bone marrow-derived macrophages have been transferred into naïve recipients. Because the pulsed BMMΦ responded to this treatment with the secretion of IL-33, the data support the conclusion that this cytokine is a dominant mediator in the pathway that leads to $T_{reg}$ cell activation and expansion.

Previous studies have established the connection between IL-33 and an amelioration of T cell-mediated inflammation in different mouse models that were always accompanied by an enrichment of $T_{reg}$ cells. Additionally, serum levels of IL-33 have been shown to be highly elevated upon IVIG administration in human autoimmune patients, thus making it a potent inducer of various anti-inflammatory responses. When antibodies were used to block ST2 that prevented IL-33 signaling, the inventors observed that this treatment significantly compromised the protective effect of IVIG/F241A in both a serum transfer arthritis model, as well as in the EAE model.

It is becoming increasingly clear that far from being a 'constant' domain, the Fc region of antibodies exhibit heterogeneous structures and functions. This invention disclosed herein advances the view that the conformational diversity of the Fc fragment serves as a general strategy for antibodies to shift receptor specificity in order to effect different immunological outcomes. IgG Fc dynamics are fine-tuned by protein-glycan interactions, which are in turn regulated by the sugar composition of the Fc glycan. The inventors find that a model of increased Fc glycan mobility accounts for the biophysical and functional properties associated with anti-inflammatory activity of sialylated IgG. Based on these structural and mechanistic observations, the inventors have developed a surrogate for sialylated IgG, such as F241A, which offers the benefit of greater potency and uniformity than IVIG and can be used for clinical development for both autoantibody- and T cell-mediated inflammatory diseases.

Polypeptides and Nucleic Acids

Polypeptides

As disclosed herein, this invention provides isolated polypeptides having sequences of variants of human IgG Fc that lacks a polysaccharide chain having a terminal sialic acid connected to a galactose moiety through the α2,6 linkage at the aforementioned Asn$^{297}$. Such non-sialylated IgG Fc variants may be either derived from a naturally occurring antibody or expressed in a cell line.

In one embodiment, the Fc region includes one or more substitutions of the hIgG1 amino acid sequence. While not limited thereto, exemplary IgG1 Fc regions are provided as follows:

```
Fc of hIgG1 (starting from amino acid 210 in Kabat
system):
        (SEQ ID NO: 1; F241 and F243 are underlined)
KVDKRVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGK

Fc of hIgG1 FA241:
                                       (SEQ ID NO: 2)
KVDKRVEPKSCDKTHTCPPCPAPELLGGPSVALFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGK

Fc of hIgG1 FA243:
                                       (SEQ ID NO: 3)
KVDKRVEPKSCDKTHTCPPCPAPELLGGPSVFLAPPKPKDTLMISRTPEV

TCVVVDVSHEDPEVKFNWYVDGVEVHNAKTKPREEQYNSTYRVVSVLTVL
```

-continued

```
HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGK
```

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation). The peptide, polypeptide, or protein "of this invention" include recombinantly or synthetically produced versions having the particular domains or portions that bind to DC-SIGN, FcγRIIA, and FcγRIIB The term also encompasses polypeptides that have an added amino-terminal methionine (useful for expression in prokaryotic cells).

An "isolated" polypeptide or protein refers to a polypeptide or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods. A functional equivalent of IgG Fc refers to a polypeptide derivative of IgG Fc, e.g., a protein having one or more point mutations, insertions, deletions, truncations, a fusion protein, or a combination thereof. It retains substantially the activity of the IgG Fc, i.e., the ability to bind to the respective receptor and trigger the respective cellular response. The isolated polypeptide can contain SEQ ID NO: 2. In general, the functional equivalent is at least 75% (e.g., any number between 75% and 100%, inclusive, e.g., 75%, 80%, 85%, 90%, 95%, and 99%) identical to SEQ ID NO: 2.

The "percent identity" of two amino acid sequences or of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NB LAST) can be used.

The amino acid composition of the polypeptide described herein may vary without disrupting the ability of the polypeptide to bind to the respective receptor and trigger the respective cellular response. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in, e.g., SEQ ID NO: 2, is preferably replaced with another amino acid residue from the same side chain family. Alternatively, mutations can be introduced randomly along all or part of the sequences, such as by saturation mutagenesis, and the resultant mutants can be screened for the ability to bind to the respective receptor and trigger the respective cellular response to identify mutants that retain the activity as descried below in the examples.

A polypeptide as described in this invention can be obtained as a recombinant polypeptide. To prepare a recombinant polypeptide, a nucleic acid encoding it (e.g., FA241, SEQ ID NO: 2) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Nucleic Acids

Another aspect of the invention features an isolated nucleic acid comprising a sequence that encodes the polypeptide or protein described above. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the fusion protein of this invention. For this purpose, one can operatively linked the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector includes a nucleic acid in a form suitable for expression of the nucleic acid in a host cell. Preferably the vector includes one or more regulatory sequences operatively linked to the nucleic acid sequence to be expressed.

A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein or RNA desired, and the like. The expression vector can be introduced into host cells to produce a polypeptide of this invention. A promoter is defined as a DNA sequence that directs RNA polymerase to bind to DNA and initiate RNA synthesis. A strong promoter is one which causes mRNAs to be initiated at high frequency.

Any polynucleotide as mentioned above or a biologically equivalent polynucleotide available to the artisan for the same intended purpose may be inserted into an appropriate expression vector and linked with other DNA molecules to form "recombinant DNA molecules" expressing this receptor. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA. It is well within the purview of the artisan to determine an appropriate vector for a particular use.

A variety of mammalian expression vectors may be used to express the above-mentioned IgG Fcs in mammalian cells. As noted above, expression vectors can be DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. Expression vectors may include, but are not limited to, cloning vectors, modified cloning vectors, specifically designed plasmids or viruses. Commercially available mammalian expression vectors which may be suitable, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also within the scope of this invention is a host cell that contains the above-described nucleic acid. Examples include E. coli cells, insect cells (e.g., using baculovirus expression vectors), yeast cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, e.g., using T7 promoter regulatory sequences and T7 polymerase.

All of naturally occurring IgG Fcs, genetic engineered IgG Fcs, and chemically synthesized IgG Fcs can be used to practice the invention disclosed therein. IgG Fc obtained by recombinant DNA technology may have the same amino acid sequence as [FA241] SEQ ID NO: 2) or an functionally equivalent thereof. The term "IgG Fc" also covers chemically modified versions. Examples of chemically modified IgG Fc include IgG Fcs subjected to conformational change, addition or deletion of a sugar chain, and IgG Fc to which a compound such as polyethylene glycol has been bound.

One can verify the efficacy of a polypeptide/protein thus-made using an animal model, such as a transgenic mouse, as described below. Any statistically significant increase in in vivo expression of IL-33 basophils or expression of the FcγRIIB receptor on effector macrophages indicates the polypeptide/protein is a candidate for treating the disorders mentioned below. In one embodiment, the above described assays may based on measurement of a binding to DC-SIGN protein or DC-SIGN$^{(+)}$ cells. The art is replete with various techniques available to the artisan that will be suitable to measuring the ability of a compound to a DC-SIGN or to DC-SIGN$^{(+)}$ cells and related changes in expression of a gene regulated by the DC-SING pathway, such as IL-33. The artisan will be capable of mixing and matching these various research tools without undue experimentation. Once purified and tested by standard methods or according to the assays and methods described in the examples below, non-sialylated IgG Fc variants can be included in pharmaceutical composition for treating inflammatory disorders.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

As used herein, the term "Fc fragment" or "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification."

Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 75 or 80% homology with a native sequence Fc region and/or with an Fc region of a parent polypeptide, and more preferably at least about 90% homology therewith, more preferably at least about 95% homology therewith, even more preferably, at least about 99% homology therewith.

The terms "Fc receptor" or "FcR" are used to describe a receptor that binds to the Fc region of an antibody. In one embodiment of the invention, FcR is a native sequence human FcR. In another embodiment, FcR, including human FcR, binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, Annu Rev Immunol, 15, 203-234 (1997); FcRs are reviewed in Ravetch and Kinet, Annu Rev Immunol, 9, 457-92 (1991); Capel et al., Immunomethods, 4, 25-34 (1994); and de Haas et al., J Lab Clin Med, 126, 330-41 (1995), Nimmerjahn and Ravetch 2006, Ravetch Fc Receptors in Fundemental Immunology, ed William Paul 5th Ed. each of which is incorporated herein by reference).

The term "native" or "parent" refers to an unmodified polypeptide comprising an Fc amino acid sequence. The parent polypeptide may comprise a native sequence Fc region or an Fc region with pre-existing amino acid sequence modifications (such as additions, deletions and/or substitutions).

Compositions

Within the scope of this invention is a composition that contains a suitable carrier and one or more of the agents described above, such as the non-sialylated IgG Fc variants. The composition can be a pharmaceutical composition that contains a pharmaceutically acceptable carrier or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

The above-described composition, in any of the forms described above, can be used for treating disorders characterized by inflammation. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, TWEENS or SPANS or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas. The topical composition is useful for treating inflammatory disorders in the skin, including, but not limited to eczema, acne, rosacea, psoriasis, contact dermatitis, and reactions to poison ivy.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition. The topical composition may be a cosmetic or dermatologic product in the form known in the art for topical or transdermal applications, including solutions, aerosols, creams, gels, patches, ointment, lotion, or foam.

Treatment Methods

The described invention provides methods for treating in a subject an inflammatory disorder. The term "inflammatory disorder" refers to a disorder that is characterized by abnormal or unwanted inflammation, such as an autoimmune disease. Autoimmune diseases are disorders characterized by the chronic activation of immune cells under non-activating conditions. Examples include psoriasis, inflammatory bowel diseases (e.g., Crohn's disease and ulcerative colitis), rheumatoid arthritis, psoriatic arthritis, multiple sclerosis, lupus, type I diabetes, primary biliary cirrhosis, and transplant.

Other examples of inflammatory disorders that can be treated by the methods of this invention include asthma, myocardial infarction, stroke, inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), acute respiratory distress syndrome, fulminant hepatitis, hypersensitivity lung diseases (e.g., hypersensitivity pneumonitis, eosinophilic pneumonia, delayed-type hypersensitivity, interstitial lung disease (ILD), idiopathic pulmonary fibrosis, and ILD associated with rheumatoid arthritis), and allergic rhinitis. Additional examples also include myasthenia gravis, juvenile onset diabetes, glomerulonephritis, autoimmune throiditis, ankylosing spondylitis, systemic sclerosis, acute and chronic inflammatory diseases (e.g., systemic anaphylaxia or hypersensitivity responses, drug allergies, insect sting allergies, allograft rejection, and graft-versus-host disease), and Sjogren's syndrome.

In one embodiment, the invention provides methods for treating a T cell-mediated disease. As used herein a T cell-mediated disease refers to any inflammatory disorder characterized by an abnormal low level of regulatory T cells (Treg cells) or by abnormally activated Teffector cells. Examples of this disease include, but are not limited to, multiple sclerosis, Type I diabetes, Myasthenia gravis, rheumatoid arthritis (RA), systemic lupus erythematosus (SLE), and Psoriasis (see e.g., Fundamental Immunology, Paul, W., ed., 7th edition, Lippincott Williams & Wilkins, 2012, p 832).

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

A subject to be treated for an inflammatory disorder can be identified by standard diagnosing techniques for the disorder. Optionally, the subject can be examined for the level or percentage of one or more of cytokines or cells a test sample obtained from the subject by methods known in the art. If the level or percentage is at or below a threshold value (which can be obtained from a normal subject), the subject is a candidate for treatment described herein. To confirm the inhibition or treatment, one can evaluate and/or verify the level or percentage of one or more of the above-mentioned cytokines or cells in the subject after treatment.

"Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder.

An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The agent can be administered in vivo or ex vivo, alone or co-administered in conjunction with other drugs or therapy, i.e., a cocktail therapy. As used herein, the term "co-administration" or "co-administered" refers to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound or agent is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds/agents available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

EXAMPLES

Example 1: General Methods and Materials

This example describes general methods and materials used in Examples 2-8 below.

Mice

Six-to-ten week old, sex and age matched C57BL/6, SIGN-R1$^{-/-}$, and SIGN-R1$^{-/-}$hDC-SIGN$^+$ mice were used for all experiments in compliance with federal laws and institutional guidelines approved by The Rockefeller University. SIGN-R1$^{-/-}$ mice were bred to CD11c-hDC-SIGN$^+$ mice to generate SIGN-R1$^{-/-}$hDC-SIGN$^+$ mice. KRN T cell receptor transgenic mice were on a C57BL/6 background and bred to NOD mice to create K/BxN mice (Korganow et al. *Immunity* 1999, 10(4): 451-461). K/BxN serum was prepared by collecting blood samples from K/BxN mice. The serum was separated from blood and pooled and frozen into aliquots for further usage. In order to induce serum transfer arthritis, 200 µl of pooled K/BxN serum was injected intraperitoneally. Severity of arthritis was scored by clinical examination of the paws. The addition of all four paws indices reflected the severity of disease. 0 is unaffected, 1 is swelling of one joint, 2 is swelling of more than one joint, and 3 is severe swelling of the entire paw. In all experiments, groups of 4-5 mice were used and means and standard error of the mean (SEM) are plotted in graphs.

Reagent and Treatments

IVIG (Octagam, Octapharma) and F241A (Merck) were used at concentrations indicated in each figure legend. IVIG-Fc and IVIG-F(ab')$_2$ preparations were prepared by papain digestion of IVIG for 2 hours at 37° C. Desialylation of IVIG and F241A was performed by neuraminidase treatment. 100 mg of antibody preparation was incubated with 700 Units Neuraminidase (NEB) for 20 hours at 37° C. Antibodies were purified by Protein-G affinity purification and dialyzed against PBS before injection. Sialic acid contents of all antibody preparations were verified by SNA lectin blotting using SNA-biotin (Vector laboratories). All IVIG and F241A preparations were administered intravenously (i.v.).

Basophils were depleted by daily i.p. injection with 10 µg anti-FcεRI (MAR-1, eBioscience) or hamster IgG isotype control (Sigma) for 4 consecutive days.

$T_{reg}$ cells were depleted by i.p. administration of 400 µg of anti-CD25 (Setiady et al. *Eur J Immunol* 2010, 40(3): 780-786) (PC61, BioXcell) 3 days before EAE induction as well as one day after each IVIG/F241A injection until the end of the experiment.

Blocking of the IL-33 receptor ST2 was achieved by i.v. injections of 100 µg of anti-T1/ST2 (DJ8, MD Biosciences) on day 0 as well as every fifth day post EAE induction.

For cytokine treatment, mice received a single i.v. injection of 2.5 µg of IL-4ic (Peprotech) or 0.5 µg IL-33 i.p. on 4 consecutive days or every two days in EAE experiments.

IL-6 serum levels were measured by an in vivo cytokine capture assay as described (Finkelman et al. *Curr Protoc Immunol* 2003, Chapter 6: Unit 6.28). IL-33 in cell culture supernatants was detected and measured by ELISA, respectively, as suggested by the manufacturer (eBioscience).

Flow Cytometry

In order to analyze lymphocytes and bone marrow cells, single cell suspensions were prepared from spleens, lymph nodes, and bone marrow. After red blood cell lysis cells were stained with the respective antibodies and analyzed using a FACSCalibur (BD Biosciences). The antibodies used for murine cell stainings were anti-CD4 (GK1.5), anti-Foxp3 (FJK-16s), anti-IFNγ (XMG1.2) from eBiosciences, anti-CD25 (PC61), anti-IL-17A (TC11-18H10.1), anti-CD209 (9E9A8), anti-Helios (22F6), anti-CD11c (N418), anti-F4/80 (BM8) from BioLegend and anti-T1/ST2 (MD Biosciences).

Differentiation of Bone Marrow-Derived Macrophages and Transfers

Bone marrow cells were isolated from femurs and tibias, cultured in 10-cm plates in DMEM supplemented with 20% fetal bovine serum, 2% penicillin/streptomycin (Invitrogen), 1% L-glutamine 200 mM (Invitrogen), 0.1% β-mercaptoethanol and M-CSF (40 ng/mL, Peprotech) for 5-7 days at 37° C. Flow cytometry was used to analyze bone marrow-derived macrophages (BMMΦ) in the cell cultures (>90% CD11b$^+$ F4/80$^+$ cells). Cells were recovered from plates, washed and seeded in fresh tissue culture plates, and subsequently pulsed with PBS, IVIG (15 mg/mL) or F241A (80 µg/ml) for 3 hours at 37° C. Cells were then extensively washed and 1×10$^6$ macrophages were administered intravenously to recipient mice. One hour post transfer, mice were challenged with K/BxN sera.

Quantitative Real-Time PCR

Total RNA was isolated from bone marrow-derived macrophages using the RNeasy Mini Kit (Qiagen) and reverse transcribed with Superscript III Reverse Transcriptase (Invitrogen). Quantitative PCR was performed to measure IL-33 mRNA levels using a C1000 Touch Thermal Cycler (BioRad) with primer sets for IL-33 (5'-TCACTGCAG-GAAAGTACAGCA-3' (forward, SEQ ID NO: 4) and 5'-AGTAGCACCTGGTCTTGCTC-3' (reverse, SEQ ID NO: 5)) and Gapdh (5'-ACAGTCCATGCCATCACTGCC-3' (forward, SEQ ID NO: 6) and 5'-GCCTGCTTCAC-CACCTTCTTG-3' (reverse, SEQ ID NO: 7)). Gene expression levels were calculated by normalization to Gapdh mRNA levels.

In Vitro T$_{reg}$ Cell Differentiation

Single cell suspensions were prepared from spleens and lymph nodes of naïve C57BL/6 wild-type mice. Naïve CD4$^+$ T cells were isolated by magnetic cell separation (Miltenyi Biotec) and cultured for 3 days in RPMI supplemented with 10% fetal bovine serum, 2% penicillin/streptomycin (Invitrogen), 1% L-glutamine 200 mM (Invitrogen) and 0.1% β-mercaptoethanol, anti-CD3 (17A2, eBioscience) and anti-CD28 (37.51, eBioscience) antibodies in 24-Well cell culture plates that were coated with anti-Hamster IgG (MP Bio). For T$_{reg}$ cell differentiation, TGF-β (2.5 ng/mL, Peprotech) was added. IL-33 (1 ng/mL, BioLengend) or IL-23 (20 ng/mL Peprotech) was added to the cell cultures as indicated in the figure legend. On day 3, cells were recovered and T$_{reg}$ cells (CD4$^+$CD25$^{30}$Foxp3$^+$) were analyzed by FACS.

T Cell Transfer Colitis

For T cell transfer colitis, 5×10$^5$ naïve CD4$^+$ CD45RB$^{hi}$CD25$^-$ T cells from C57BL/6 wild-type animals were sorted and injected i.p. into C57BL/6 Rag1$^{-/-}$ recipient mice. Body weight loss was measured twice a week and used as a means of disease severity.

Experimental Autoimmune Encephalomyelitis

Six-to-eight week old mice C57BL/6, SIGN-R1$^{-/-}$, or SIGN-R1$^{-/-}$ hDC-SIGN$^+$ mice were immunized subcutaneously with 200 µl of an emulsion consisting of 200 µg MOG$_{35-55}$ peptide (MEVGWYRSPFSRVVHLYRNGK, AnaSpec, SEQ ID NO: 8) emulsified in complete Freund's adjuvant (Difco Laboratories). On day 0 and 2, mice received 200 µg of pertussis toxin (List Biological) intraperitoneally. Development of disease was monitored daily according to the following criteria: 0—No clinical signs; 0.5—Partially limp tail; 1—Paralyzed tail; 2—Loss in coordinated movement; hind limb paresis; 2.5—One hind limb paralyzed; 3—Both hind limbs paralyzed; 3.5—Hind limbs paralyzed and hunched back; 4—Severely hunched back and weakness in forelimbs; 4.5—Forelimbs paralyzed; 5—Moribund (Stromnes et al. *Nat Protoc* 2006, 1(4): 1810-1819).

Example 2 F241A Mimics Sialylated IgG-Fc and Protects from Autoantibody Induced Inflammation The crystal structures of non-sialylated and sialylated IgG molecules show differences in the orientation of the heavy chains. While non-sialylated IgG (G0F-form) remains in an open conformation and provides a structure capable of interacting with type I Fc receptors, the sialylated IgG (G2FS2-form) is more flexible allowing alternate conformations (open and closed) (Ahmed et al. *J Mol Biol* 2014, 426(18): 3166-3179) enabling it to bind to type II Fc receptors (Sondermann et al. *Proc Natl Acad Sci USA* 2013, 110(24): 9868-9872). As shown in FIG. 1a, the aromatic side chains of F241 in an asial Fc structure are stacked with respect to each other (FIG. 1a, left panel). In this orientation, the phenylalanine side chain forms a hydrophobic interaction with sugar residues in the α1,3 arm of the Fc glycan. Surprisingly, the aromatic ring of F241 in the sial Fc structure exhibits a near 90° rotation relative to the aromatic ring of F241 in the asial Fc structure (FIG. 1a, right panel). This suggests that upon sialylation, the interaction between F241 and the α1,3 arm of the Fc glycan may be disrupted, which potentially contributes to the observed changes in antibody structure and function.

Figure 8:
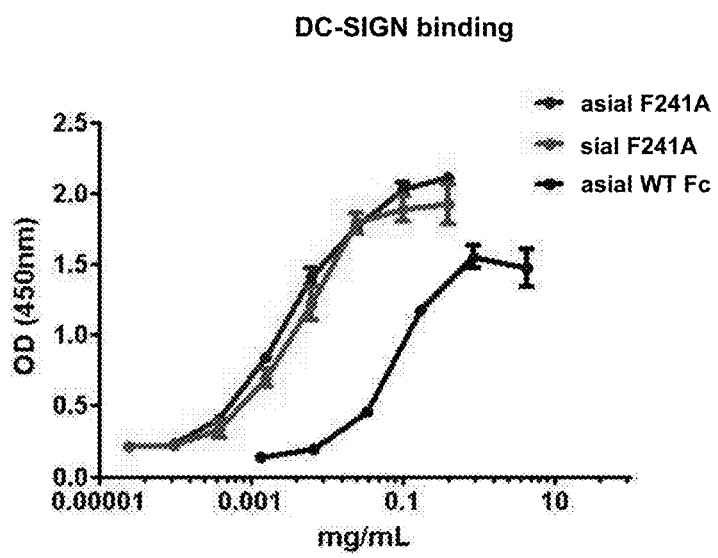
FIG. 8 shows that F241A binds to DC-SIGN independent of sialylation. Recombinant DC-SIGN was immobilized and binding affinity of asialylated (asial F241A), sialylated F241A (sial F241A) and asialylated wild-type Fc (asial WT Fc) was measured by ELISA.

Hence, to mimic this disruption in protein-glycan interaction, the inventors introduced an alanine point mutation at residue F241 (F241A) and determined how this mutation altered the activity of sial and asial Fc. The inventors produced α2,6-sialylated F241A Fc by expressing the recombinant protein in 293 cells stably overexpressing the glycosyltransferases ST6GalI and β4GalTI. For comparison, a fraction of this sial F241A Fc preparation was subsequently treated with neuraminidase to remove sialic acid yielding asial F241A Fc. The inventors confirmed the sialylation status of both F241A Fc preparations by lectin blotting. The inventors next verified that sial F241A Fc retained DC-SIGN binding activity in an ELISA format as demonstrated by increased receptor binding affinity relative to asial WT Fc (FIG. 8). However, neuraminidase treatment of F241A Fc did not abolish DC-SIGN binding establishing that the F241A mutation conferred DC-SIGN binding activity independent of sialic acid.

To determine if the F241A mutation resulted in functional DC-SIGN binding and signaling, the inventors investigated the ability of F241A and sFc to induce IL-33 expression in DC-SIGN expressing bone marrow-derived macrophages (BMMΦ). Only sFc induces IL-33 expression in these cells, while both sialylated and asialylated F241A Fc induced IL-33 expression in BMMΦ in a DC-SIGN-dependent manner (FIG. 1b). Furthermore, hDC-SIGN+ BMMΦ stimulated with asial F241A Fc, as well as sFc, suppressed footpad swelling when transferred to mice challenged with arthritogenic K/BxN serum in a DC-SIGN dependent manner (FIG. 1c). Furthermore, protection was only achieved with sialylated wild-type Fc, whereas the Fc mutant F241A was capable of protecting mice, even when non-sialylated (FIG. 1d). Thus, the F241A mutation recapitulates several Fc functions in assays developed to measure sial Fc activity.

Figures 2A, 2B, 2C:
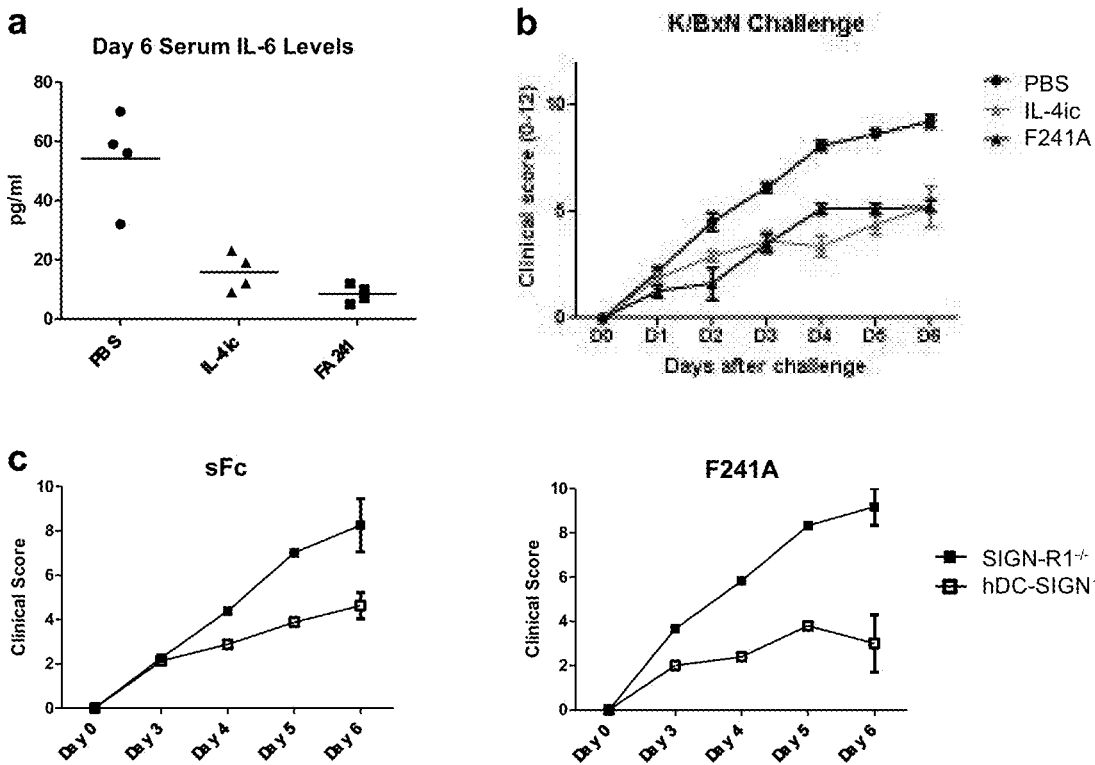
FIGS. 2A, 2B and 2C show that F241A induces anti-inflammatory responses through engagement of type II Fc receptors. (a) C57BL/6 wild-type mice were treated with PBS, IL-4ic or F241A (0.033 g/kg) and were challenged one hour later with K/BxN sera. Blood was collected from these mice 6 days post treatment and serum IL-6 levels were analyzed by ELISA. (b) Clinical scores of mice were monitored reflecting the severity of serum-induced arthritis. (c) SIGN-R$^{-/-}$ and hDC-SIGN$^+$ mice were challenged with K/BxN serum and treated with sialylated wild-type Fc (sFc) or F241A (both 0.033 g/kg). Development of disease was monitored daily until day 6 post disease induction.

To further define the activity of F241A as an anti-inflammatory molecule, the inventors challenged C57BL/6 wild-type mice with K/BxN sera and treated them either with PBS, IL-4ic or asialylated F241A (0.033 g/kg). Serum IL-6 levels were significantly reduced in mice that received IL-4ic or F241A (FIG. 2a). Consistent with this observation, IL-4ic- and F241A-treated mice showed reduced clinical signs of arthritis (FIG. 2b), showing that F241A is sufficient to suppress inflammation comparable to IVIG and sFc (Kaneko et al. *Science* 2006, 313(5787): 670-673, and Anthony et al. *Science* 2008, 320(5874): 373-376).

To confirm that this suppression by F241A is type II FcR dependent, the inventors used SIGN-R1$^{-/-}$ or SIGN-R1$^{-/-}$ hDC-SIGN+ recipients. Mice received either sialylated wild-type Fc or neuraminidase-treated non-sialylated F241A (both 0.033 g/kg) and were challenged with K/BxN sera. Suppression of arthritic inflammation was achieved by both preparations; however, only mice that expressed the BAC transgene human DC-SIGN (hDC-SIGN+) were protected (FIG. 2c), demonstrating that the presence of the type II Fc receptor SIGN-R1 or its human orthologue DC-SIGN, respectively, is required for the immunomodulatory effect induced by sialylated Fc and F241A.

Figures 3A, 3B, 3C:
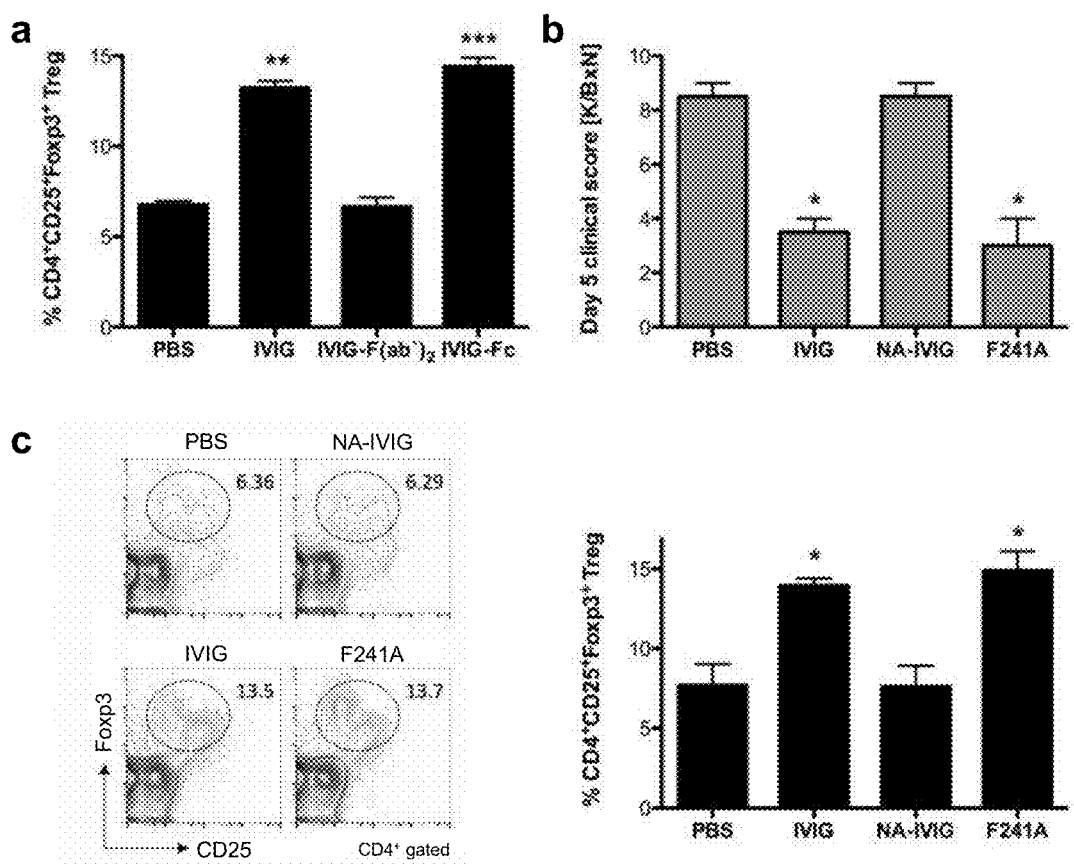
FIGS. 3A, 3B, and 3C show that sFc/F241A activates and expands T$_{reg}$ cells. (a) C57BL/6 wild-type mice received intravenous injections of IVIG (1 g/kg), IVIG-F(ab')$_2$ (0.66 g/kg), IVIG-Fc (0.33 g/kg) or PBS as control. On day 5 post injection T$_{reg}$ cell numbers in spleens were analyzed by flow cytometry. (b) K/BxN-challenged C57BL/6 wild-type mice were given IVIG (1 g/kg), neuraminidase-treated IVIG (NA-IVIG) (1 g/kg), non-sialylated F241A (0.033 g/kg) or PBS as control. Clinical signs of arthritis were monitored. (c) On day 5 post treatment mice were euthanized and T$_{reg}$ cells in spleens were analyzed by flow cytometry. Means+/−SEM are plotted; *p<0.05; p<0.01; *p<0.001 determined by Tukey's post-hoc test.

Sialic acid can be linked to the penultimate galactose of the complex, bi-antennary Fc glycan in either α2,3, α2,6 or α2,8 conformations. The inventors have previously reported that only the α2,6-linked glycoform of sialic acid is biologically active (Anthony et al. *Science* 2008, 320(5874): 373-376). Previous modeling data on the structural analysis of different Fc sialoforms (Sondermann et al. *Proc Natl Acad Sci USA* 2013, 110(24): 9868-9872) predicted that the Glu318/Lys340 pocket at the Cγ2-Cγ3 interface was required for the biological activity of α2,6-sial Fc and could uniquely accommodate this glycoform, while the α2,3 linked sialic acid would be sterically inhibited from fitting into this pocket. To test this prediction, the inventors introduced an E318N point mutation into IgG1 Fc and compared its properties, when α2,6 sialylated, to wild-type α2,6-sial Fc. While comparable degrees of sialylation were achieved with mutant as compared to the wild-type, only the wild-type sialylated Fc was capable of stimulating IL-33 expression in hDC-SIGN+ BMMΦ (FIG. 9a). Mice receiving BMMΦ stimulated with α2,6-sial wild-type Fc, but not α2,6-sial E318N Fc, exhibited reduced clinical signs of disease (FIG. 9b), as well as lower levels of IL-6 (FIG. 3c).

Together these results define both F241 and E318 as residues that contribute to the anti-inflammatory activity of α2,6-sial Fc.

Example 3 Sialylated Fc/F241A Activates Treg Cells

Recent studies in patients and in animal models suggest that administration of IVIG can result in an expansion of $T_{reg}$ cells (Ephrem et al. Blood 2008, 111(2): 715-722, and Bayry J et al. *Rheumatol*, vol. 39: Canada, 2012, pp 450-451), effectively dampening T cell-dependent autoimmune reactions by increasing the number and the suppressive capacity of $T_{reg}$ cells (Kessel et al. *J Immunol* 2007, 179(8): 5571-5575). To determine which component of an IVIG preparation may be responsible for this effect, the inventors used IVIG (1 g/kg), F(ab')2 (0.66 g/kg) or Fc (0.33 g/kg) preparations of IVIG and administered them intravenously at equimolar concentrations into C57BL/6 wild-type mice. Four days post injection the inventors analyzed the percentage of splenic CD4+CD25+Foxp3+ $T_{reg}$ cells by flow cytometry. In comparison to PBS-treated mice, administration of intact IVIG or its Fc fragments led to a two-fold expansion of $T_{reg}$ cells and was abrogated by using IVIG-F(ab')2 (FIG. 3a).

We next determined the role of Fc sialylation in $T_{reg}$ cell expansion in an ongoing inflammatory response. K/BxN-challenged C57BL/6 mice were treated either with PBS, IVIG (1 g/kg), neuraminidase-treated non-sialylated IVIG (NA-IVIG)(1 g/kg) or F241A (0.033 g/kg) and evaluated for disease progression and $T_{reg}$ cell expansion. As observed previously (Schwab et al. *Eur J Immunol* 2014, 44(5): 1444-1453, and Anthony et al. *Nature* 2011, 475(7354): 110-113), clinical scores of arthritis showed that IVIG and F241A, but not non-sialylated IVIG, protected mice from arthritis (FIG. 3b). $T_{reg}$ cell expansion was observed in IVIG and F241A treated mice, but not in asial-IVIG treated mice (FIG. 3c) suggesting that the $T_{reg}$ cell subset becomes selectively expanded by sialylated Fc and F241A, respectively.

Example 4 IVIG-/F241A-Activated $T_{reg}$ Cells Suppress CD4+ T Cell Responses

Figures 4A, 4B, 4C, 4D, 4E, 4F:
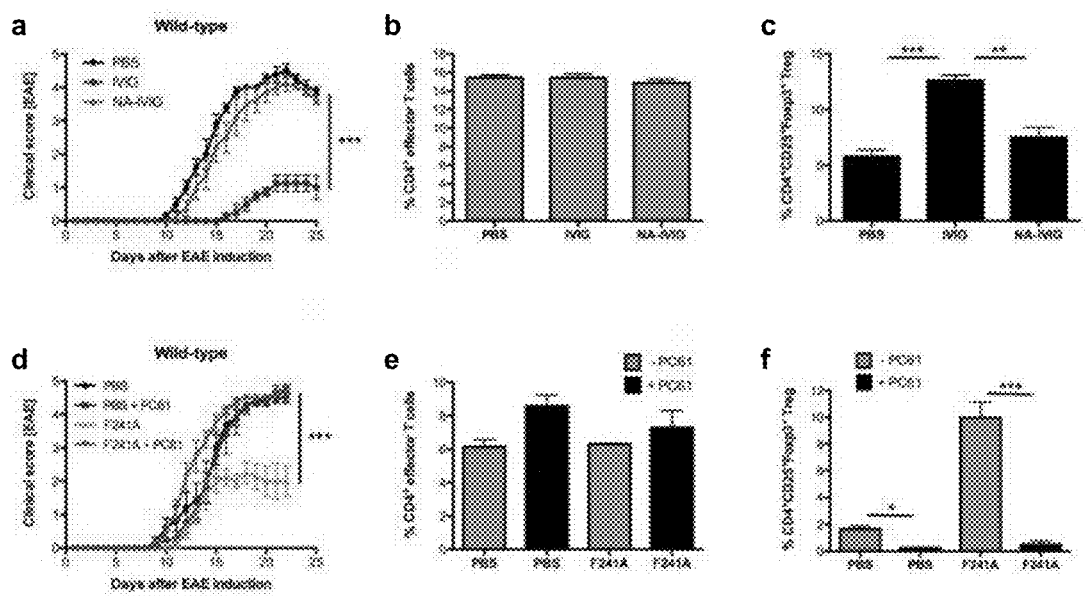
FIGS. 4A, 4B, 4C, 4D, 4E and 4F show that IVIG-/F241A-activated T$_{reg}$ cells efficiently suppress T cell-mediated autoimmunity in experimental autoimmune encephalomyelitis (EAE) mice. (a) C57BL/6 wild-type mice were immunized with MOG$_{35-55}$ peptide to induce EAE. Starting on day five post EAE induction mice received intravenous injections of PBS, IVIG (1 g/kg) or neuraminidase-treated IVIG (NA-IVIG) (1 g/kg) every 5 days. Clinical scores of EAE are shown. (b,c) Mice were euthanized and CD4$^+$ effector T cells (b) and T$_{reg}$ cells (c) from draining lymph nodes were analyzed by flow cytometry. (d) EAE was induced in C57BL/6 wild-type mice by immunization with MOG$_{35-55}$ peptide. Every five days mice received non-sialylated F241A (0.033 g/kg) or PBS intravenously. For T$_{reg}$ cell depletion mice were given the T$_{reg}$ cell depletion antibody PC61 (400 μg) 3 days before EAE induction as well as every fifth day post induction. Clinical scores of disease are depicted. (e, f) Cells from draining lymph nodes of EAE mice were isolated and analyzed for the percentages of CD4$^+$ effector T cells (e) and T$_{reg}$ cells (f) by flow cytometry. Means+/−SEM are plotted; *p<0.05; p<0.01; *p<0.001 determined by Tukey's post-hoc test.

To evaluate whether $T_{reg}$ cell expansion in response to IVIG/F241A, is able to suppress CD4+ T cell responses, the inventors induced EAE in C57BL/6 wild-type mice by immunization with $MOG_{35-55}$ peptide emulsified in CFA. Five days post induction the mice were treated with either PBS, IVIG or NA-IVIG (both 1 g/kg) to discriminate between effects specifically triggered by sialylated IgG. Clinical scores of EAE showed that mice that received IVIG had significantly reduced clinical scores when compared to PBS-treated mice (FIG. 4a). However, when asial-IVIG (NA-IVIG) was administered, the protective effect was abolished. To determine the potential mechanistic basis for this effect, the inventors characterized cells from draining lymph nodes from treated animals and analyzed the percentages of CD4+ effector T cells. All subpopulations of CD4+ effector T cells, $T_H1$ (IFN-γ+), $T_H17$ (IL-17A+), and IFN-γ+ IL-17A+ CD4+ T cells were present at similar percentages (FIG. 4b); however, the percentages of CD4+CD25+Foxp3+ $T_{reg}$ cells were significantly elevated in mice that were given IVIG compared to PBS- or NA-IVIG-treated groups (FIG. 4c).

To assess whether protection from disease is specifically mediated through activation and expansion of $T_{reg}$ cells, the inventors tested the protective potential of F241A as a surrogate for IVIG in untreated and $T_{reg}$ cell depleted mice. $T_{reg}$ cell depletion was achieved by administration of an anti-CD25 antibody (PC61). Mice treated with F241A (0.033 g/kg) alone were protected, as compared to PBS-treated mice (FIG. 4d), which showed that F241A was equally potent in protecting from T cell responses as IVIG. However in $T_{reg}$ cell depleted mice, this protective effect was significantly reduced. FACS analysis indicated that neither F241A nor PC61 treatment significantly affected CD4$^+$ effector T cells (FIG. 4e), whereas $T_{reg}$ cell levels were reduced by PC61 treatment (FIG. 4f). Depletion of $T_{reg}$ cells thus correlated with the loss of protection from EAE observed in F241A-treated animals. To distinguish between natural (n$T_{reg}$) and inducible $T_{reg}$ (i$T_{reg}$) cells, the inventors analyzed the $T_{reg}$ cells in IVIG- and PBS-treated EAE mice for their expression of the nTreg-specific transcription factor Helios (Thornton et al. *J Immunol* 2010, 184(7): 3433-3441). The expansion of $T_{reg}$ cells did not correlate with an increase in Helios expression (FIG. 10c), which indicates that IVIG (1 g/kg), which clearly protected mice from EAE (FIGS. 10 a and b), specifically induces CD4+ CD25+ Foxp3+Helios− inducible $T_{reg}$ (i$T_{reg}$) cells.

Together these results indicate that sialylated IVIG as well as F241A lead to the activation and expansion of $T_{reg}$ cells resulting in the suppression of CD4$^+$ effector T cell responses and clinical disease in EAE.

Figures 5A, 5B, 5C, 5D:
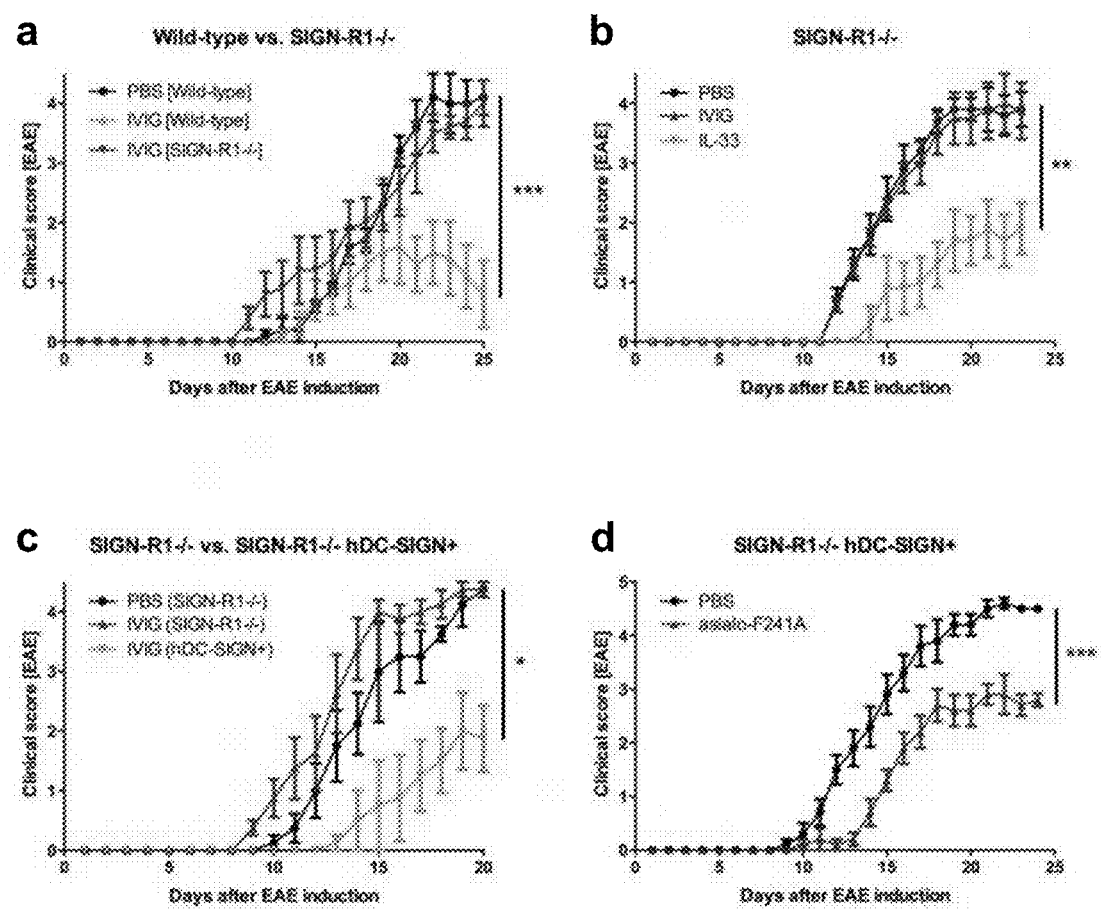
FIGS. 5A, 5B, 5C and 5D show requirement of type II Fc receptors for IVIG-/F241A-mediated T$_{reg}$ cell activation. EAE was induced in all experiments by immunization with MOG$_{35-55}$ peptide. Mice received intravenous injections on days 5, 10, 15 and 20. Clinical scores of EAE are depicted. (a) C57BL/6 wild-type and SIGN-R1$^{-/-}$ mice were treated with IVIG (1 g/kg) or PBS. (b) SIGN-R1$^{-/-}$ mice were given IVIG (1 g/kg) as mentioned above or IL-33 (0.5 μg) intraperitoneally every two days starting on day five post EAE induction. (c) SIGN-R1$^{-/-}$ and SIGN-R1$^{-/-}$ hDC-SIGN$^+$ mice were treated with PBS or IVIG (1 g/kg). (d) SIGN-R1$^{-/-}$ hDC-SIGN$^+$ mice received non-sialylated F241A (asialo-F241A) (0.033 g/kg) or PBS control. Means+/−SEM are plotted; *p<0.05; p<0.01; *p<0.001 determined by Tukey's post-hoc test.
Figure 11A:
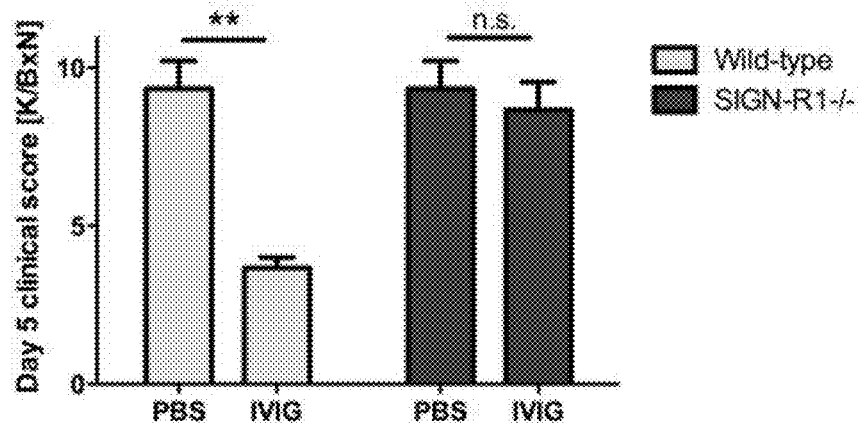
FIGS. 11A and 11B show that loss of SIGN-R1 abrogates the positive effect of IVIG on T_{reg} cells. C57BL/6 wild-type and SIGN-R1$^{-/-}$ mice were given IVIG (1 g/kg) or PBS intravenously. One hour later mice were challenged with K/BxN serum. (a) Clinical signs of arthritic disease were monitored 5 days after challenge. (b) T_{reg} cells from spleens were analyzed by flow cytometry. Means+/−SEM are plotted: **p<0.01 determined by Student's t test.
Figure 11B:
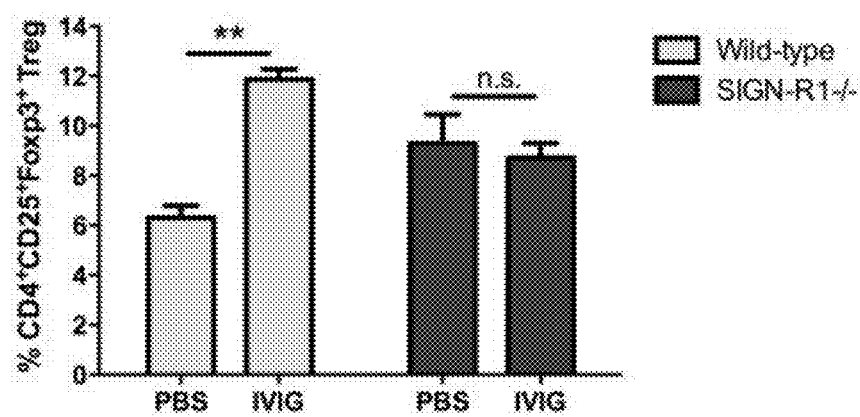

Example 5 Type II Fc Receptors are Required for sFc-Mediated Protection from EAE The requirement of the type II Fc receptors SIGN-R1 and hDC-SIGN for sFc-induced suppression of inflammation has been extensively studied in the context of autoantibody-mediated diseases and for the stimulation of IL-33 production (Anthony et al. *Nature* 2011, 475(7354): 110-113). The inventors therefore examined the requirement for the type II Fc receptor, SIGN-R1, for sFc-mediated $T_{reg}$ cell stimulation. EAE was induced in C57BL/6 wild-type or SIGN-R1$^{-/-}$ mice and then treated with IVIG (1 g/kg) or PBS as control. While wild-type mice were again protected from EAE by IVIG, this protective effect was significantly reduced in SIGN-R1 knockout mice (FIG. 5a). This is consistent with the observations that in the SIGN-R1$^{-/-}$ background IVIG (1 g/kg) neither protects from K/BxN-induced arthritis (FIG. 11a) nor induced $T_{reg}$ cell activation (FIG. 11b). By contrast, when IL-33 levels were reconstituted by administration of exogenous IL-33, SIGN-R1$^{-/-}$ mice were partially protected from EAE (FIG. 5b), which was associated with increased $T_{reg}$ cell numbers (data not shown). Similarly, transgene expression of hDC-SIGN complements the loss of SIGN-R1 (Anthony et al. *Nature* 2011, 475(7354): 110-113) and results in reduced EAE clinical scores in both IVIG (1 g/kg) and F241A (0.033 g/kg) treated mice (FIGS. 5 c and d).

Figure 12:
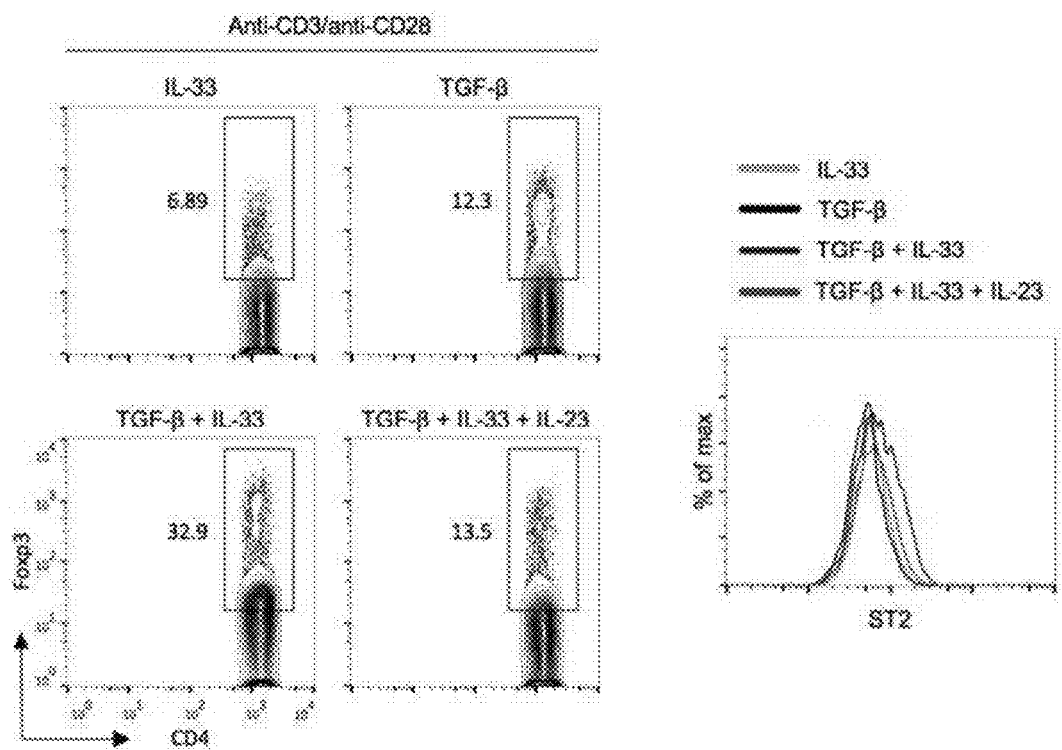
FIG. 12 shows that IL-33 synergistically contributes to T_{reg} cell differentiation in vitro. Naïve CD$^{4+}$ T cells were isolated from spleens of C57BL/6 wild-type mice. Cells were cultured three days in presence of anti-CD3/CD28. To drive T_{reg} cell differentiation TGF-β was added to the cells either alone or in combinations with IL-33 and IL-23. T_{reg} cell numbers and ST2 expression were analyzed by flow cytometry.

Example 6 IL-33 is a Critical Mediator of sFc-Triggered $T_{reg}$ Cell Activation Up-regulation of FcγRIIB on effector macrophages by sialylated Fc critically depends on production and secretion of the alarmin IL-33 (Anthony et al. *Nature* 2011, 475 (7354): 110-113). Moreover recent findings indicated that IL-33 itself has a positive effect on $T_{reg}$ cell stimulation and activation (Turnquist et al. *J Immunol* 2011, 187(9): 4598-4610, and Matta et al. *J Immunol* 2014, 193(8): 4010-4020) and thereby contributes to the suppression of inflammation in a mouse model of experimental colitis (Schiering et al. *Nature* 2014, 513(7519): 564-568). To test the possibility that sFc-induced production of IL-33 may also contribute to $T_{reg}$ cell stimulation, the inventors observed naïve CD4$^+$ T cells that were isolated from C57BL/6 wild-type mice and cultured for three days in the presence of anti-CD3, anti-CD28 antibodies and TGF-β to specifically drive $T_{reg}$ cell differentiation. The cells were either left untreated or treated in combinations with IL-33 and IL-23. Flow cytometric analysis of the percentages of CD4$^+$Foxp3$^+$ $T_{reg}$ cells in the cultures showed that addition of IL-33 had a synergistic effect on $T_{reg}$ cell differentiation as well as on Foxp3 expression (FIG. 12) as was previously reported by Schiering and coworkers (Schiering et al. *Nature* 2014, 513(7519): 564-568). Moreover IL-33 induced up-regulation of the IL-33 receptor ST2 on $T_{reg}$ cells. Addition of IL-23 to the $T_{reg}$ cell culture counteracted the effect of IL-33 (FIG. 12), consistent with IL-23 being a negative regulator of ST2 (Schiering et al. *Nature* 2014, 513(7519): 564-568, and Izcue et al. *Immunity* 2008, 28(4): 559-570).

Figures 6A, 6B, 6C, 6D, 6E, 6F, 6G:
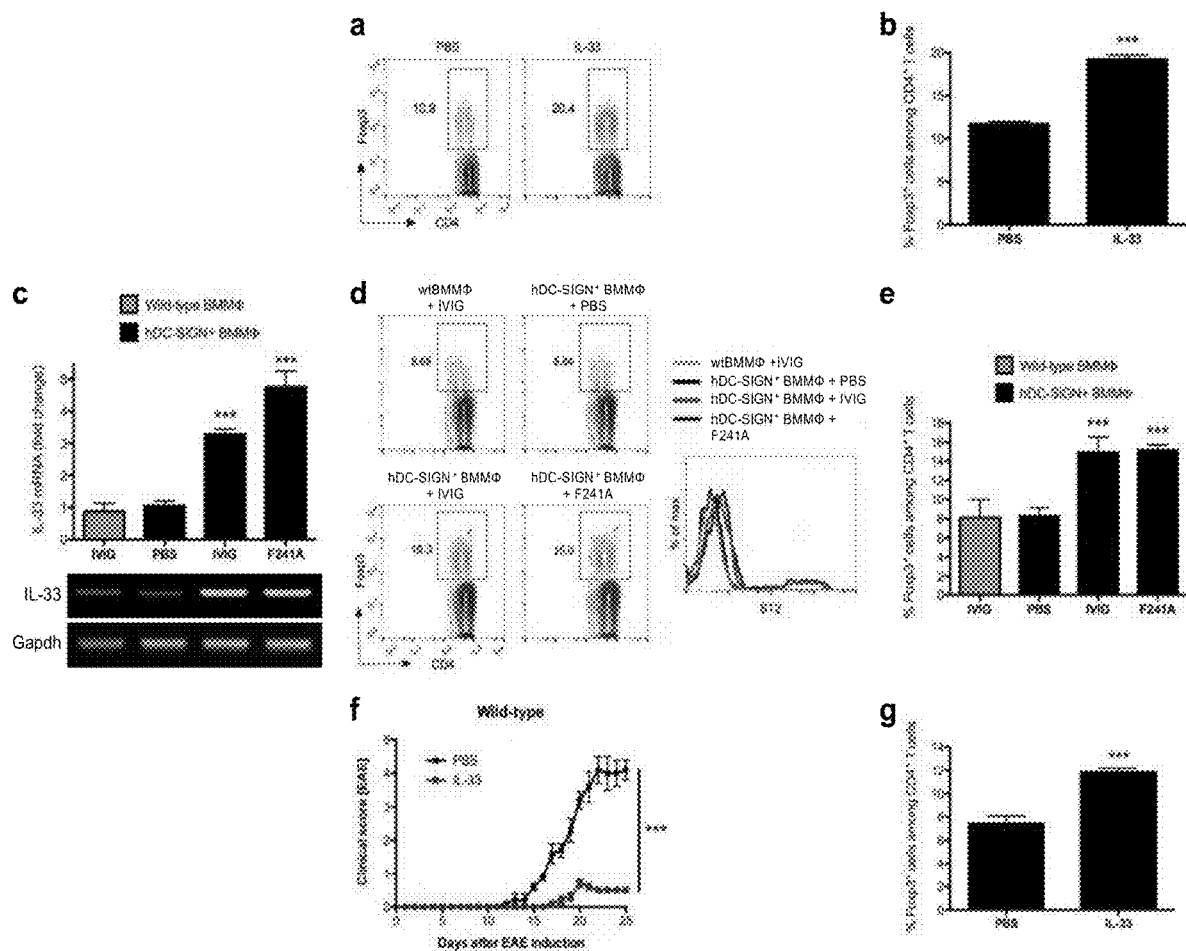
FIGS. 6A, 6B, 6C, 6D, 6E, 6F and 6G show that F241A-induced IL-33 production activates T$_{reg}$ cells. (a, b) C57BL/6 wild-type mice were given IL-33 (0.5 μg) intraperitoneally on four consecutive days. On day five mice were euthanized and the percentages of splenic Tre$_g$ cells were analyzed by flow cytometry. (c) Bone marrow-derived macrophages from C57BL/6 wild-type or hDC-SIGN$^+$ mice were pulsed with PBS, IVIG or non-sialylated F241A. (c) Total RNA was isolated and used for quantitative rtPCR to measure IL-33 mRNA levels. The housekeeping gene Gapdh was used for normalization. (d, e) After treatment bone marrow-derived macrophages were extensively washed and adoptively transferred into C57BL/6 wild-type recipient mice. On day five post transfer mice were sacrificed and T$_{reg}$ cells and ST2 expression were analyzed by flow cytometry. (f) EAE was induced in C57BL/6 wild-type mice by immunization with MOG$_{35-55}$ peptide. Every two days post induction mice received IL-33 (0.5 μg i.p.). Clinical scores of disease are shown. (g) The percentages of T_{reg} cells from draining lymph nodes of EAE mice were analyzed by flow cytometry. Means+/−SEM are plotted: ***p<0.001 determined by Tukey's post-hoc test.

Next the inventors determined whether administration of IL-33 also affects $T_{reg}$ cells in vivo. IL-33 (0.5 μg) was given to C57BL/6 wild-type mice daily for four consecutive days. On day five, spleens were analyzed for $T_{reg}$ cell numbers. IL-33 administration resulted in a significant increase of $T_{reg}$ cells compared to PBS-treated control mice (FIGS. 6 a and b). hDC-SIGN$^+$ BMMΦ were pulsed either with PBS, IVIG, or non-sialylated F241A, and IL-33 expression was measured by quantitative rtPCR, showing that IVIG and F241A clearly induced IL-33 expression in a DC-SIGN-dependent manner (FIG. 6c). After treatment, BMMΦ were subsequently transferred into C57BL/6 wild-type mice. Five days post cell transfer, only mice that received IVIG- or F241A-pulsed hDC-SIGN$^+$ BMMΦ had significantly higher levels of $T_{reg}$ cells (FIGS. 6d and e). This phenotype correlated with enhanced expression of the IL-33 receptor ST2 on these cells (FIG. 6d). In addition, IL-33 treatment of EAE resulted in a significant amelioration of EAE symptoms, which correlated with an increase of $T_{reg}$ cells in draining lymph nodes (FIGS. 6 f and g).

Figures 13A, 13B, 13C:
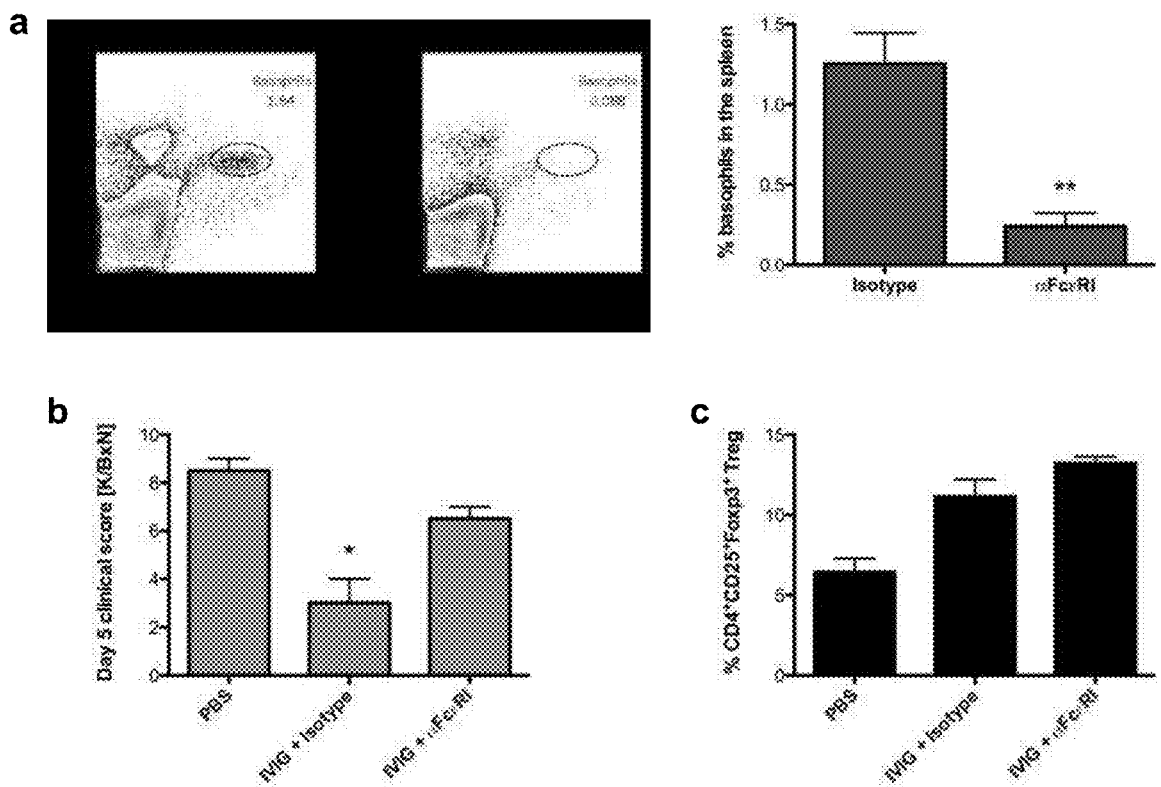
FIGS. 13A, 13B and 13C show that basophil depletion does not affect IVIG-mediated T_{reg} cell stimulation. C57BL/6 wild-type mice were treated with anti-FcεRI antibody to deplete basophils or with an isotype control. In addition, mice received IVIG (1 g/kg) or PBS and were challenged with K/BxN sera. (a) FACS analysis of splenic basophils five days after injection. (b) Clinical signs of arthritic disease were monitored on day five post disease induction. (c) Splenic T_{reg} cells were analyzed by flow cytometry. Means+/−SEM are plotted; *p<0.05; **p<0.01 determined by Tukey's post-hoc test.

Since FcγRIIB up-regulation on effector macrophages has been demonstrated to require the presence of basophils (Anthony et al. *Nature* 2011, 475(7354): 110-113), the inventors investigated whether basophils also play a role in the sFc-mediated $T_{reg}$ cell activation pathway. Mice were treated with PBS or IVIG (1 g/kg) and challenged with K/BxN serum. Mice were also treated with an anti-FcεRI antibody for depletion of basophils or with an isotype control (Sokol et al. *Nat Immunol* 2008, 9(3): 310-318). While basophil depletion (FIG. 13a), as the inventors have previously shown (Anthony et al. *Nature* 2011, 475(7354): 110-113), disrupted the protective effect of IVIG in the K/BxN arthritis model (FIG. 13b), the ability of IVIG to expand $T_{reg}$ cells was not affected (FIG. 13c). This indicates that IL-33 is required for $T_{reg}$ cell activation; however, basophils do not contribute in this pathway.

Example 7 sFc/F241A Activates Inducible $T_{reg}$ Cells Via the IL-33/ST2 Axis

Figures 7A, 7B, 7C, 7D:
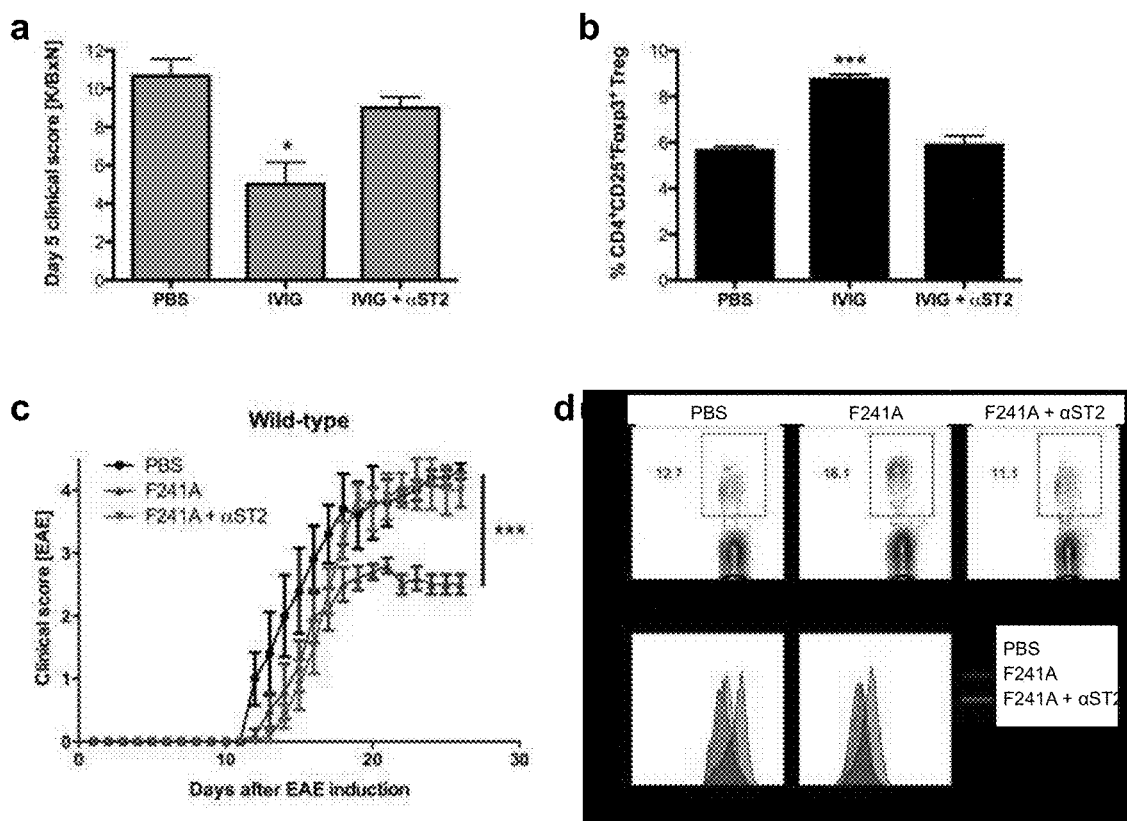
FIGS. 7A, 7B, 7C and 7D show that IVIG/F241A induces T_{reg} cell activation by signaling through the IL-33/ST2 axis. (a, b) K/BxN-challenged C57BL/6 wild-type mice were treated with PBS or IVIG (1 g/kg). In order to block IL-33 signaling mice received an anti-ST2 blocking antibody (100 μg i.v.) or isotype control. Clinical scores of RA are shown (a). On day five, post disease induction mice were sacrificed and splenic T_{reg} cells were analyzed by flow cytometry (b). (c) EAE was induced in C57BL/6 wild-type mice by immunization with MOG_{35-55} peptide. Mice were treated intravenously with PBS or non-sialylated F241A (asialo-F241A) (0.033 g/kg) four times on day 5, 10, 15 and 20. Each injection preceded an intravenous injection of an anti-ST2 blocking antibody. Shown are clinical scores of EAE. (d) EAE mice were sacrificed and cells isolated from draining lymph nodes. T_{reg} cells and their Foxp3 and ST2 expression were analyzed by flow cytometry. Means+/−SEM are plotted; *p<0.05; ***p<0.001 determined by Tukey's post-hoc test.

To further explore the mechanism of $T_{reg}$ cell expansion and activation in response to sFc and type II FcRs engagement, the inventors focused on the role of the IL-33 receptor ST2. As it has recently been reported, K/BxN-challenged mice treated with PBS or IVIG (1 g/kg) either alone or in combination with a ST2 blocking antibody indicated that blocking the IL-33 receptors reduced the protective effect of IVIG in the serum transfer arthritis model (Anthony et al. *Nature* 2011, 475(7354): 110-113) (FIG. 7a). FACS analysis of the $T_{reg}$ cell numbers in these mice revealed that inhibition of IL-33 signaling also abrogated the expansion of $T_{reg}$ cells (FIG. 7b). Similar results were observed in the EAE model, where the therapeutic effect of F241A (0.033 g/kg) was significantly reduced by blocking the IL-33 receptor (FIG. 7c) with a concomitant reduction in $T_{reg}$ cell expansion (FIG. 7d).

Figures 14A, 14B, 14C, 14D:
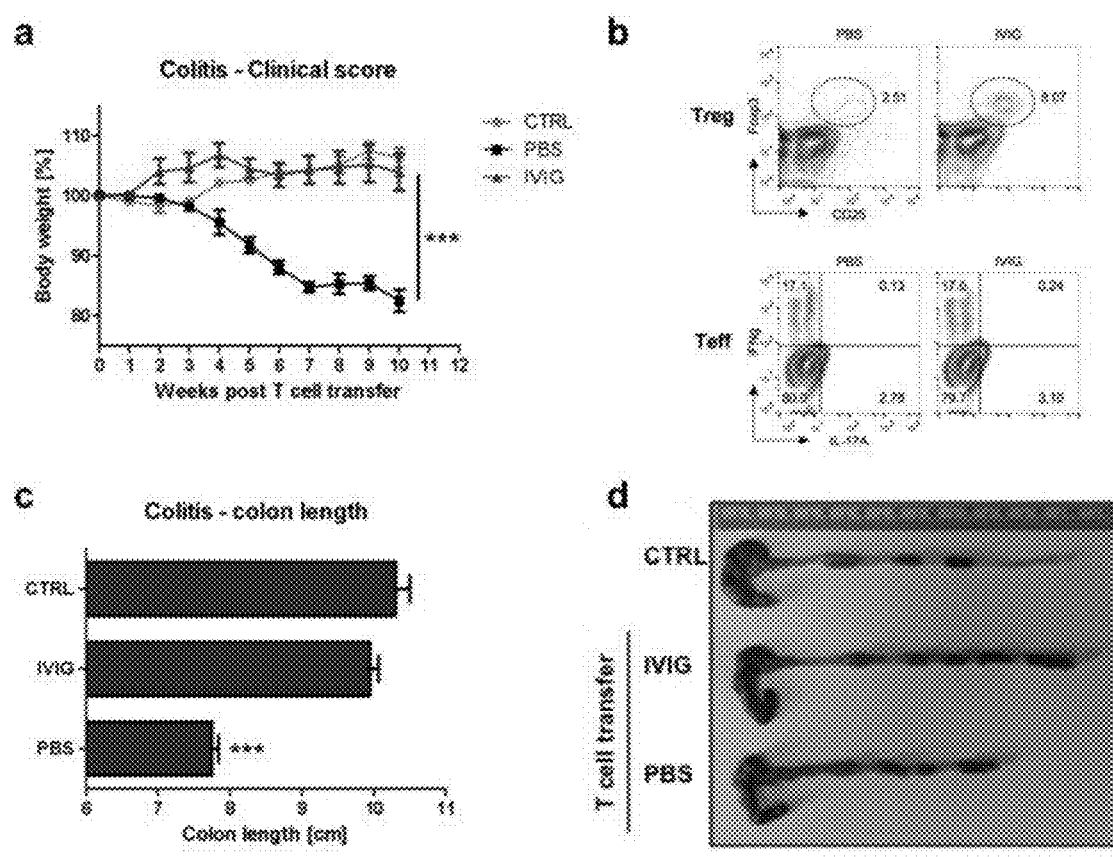
FIGS. 14A, 14B, 14C and 14D show that VIG preferentially activates iT_{reg} cells and protects from experimental colitis. C57BL/6 Rag1$^{-/-}$ mice were injected with CD4$^+$ CD45RB$^{high}$CD25$^-$ T cells in order to induce T cell transfer colitis. Mice were treated once a week with PBS or IVIG (1 g/kg) starting four weeks post T cell transfer. Rag1$^{-/-}$ control mice (CTRL) did not receive any T cells. (a) Body weight was measured once a week. Body weight loss was used as a means of disease severity. (b) Cells from draining lymph nodes were analyzed for percentages of T_{reg} cells and CD4$^+$ effector T cells by FACS. (c) Entire colons were dissected and measured. Colon shrinkage reflected disease severity and correlated with body weight loss. (d) Representative image of dissected colons as described in c. Means+/−SEM are plotted; ***p<0.001 determined by Tukey's post-hoc test.

Finally, to determine the generality of the observations on the effect of sFc on T cell-mediated diseases, the inventors used the experimental colitis mouse model and treated these mice weekly, starting four weeks post T cell transfer, with IVIG (1 g/kg) or PBS control until the end of the experiment. Body weight loss was used as a measure of disease severity, which showed that IVIG-treatment mediated protection (FIGS. 14 a, c, and d), and was again accompanied by a significant enrichment of $T_{reg}$ cells (FIG. 14b), while CD4$^+$ effector T cell levels were comparable in PBS- and IVIG-treated groups. Based on the fact that only CD4$^+$CD25$^-$ T cells have been adoptively transferred to induce acute colitis, the IVIG-expanded $T_{reg}$ cells in these mice originated from peripheral CD4$^+$ T cells and are thus i$T_{reg}$ cells.

The foregoing example and description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed is:

1. An isolated nucleic acid comprising a sequence encoding a polypeptide comprising the amino acid sequence of SEQ ID NO: 2, wherein the polypeptide has an ability to bind to a Fc receptor and an anti-inflammatory activity that is higher than that of SEQ ID NO:1.

2. A method of treating an inflammatory disease, comprising administering to a subject in need thereof a therapeutically effective amount of the nucleic acid of claim 1.

3. An expression vector comprising the nucleic acid of claim 1.

4. An isolated host cell comprising the nucleic acid of claim 1.

5. A method of producing a polypeptide, comprising culturing the host cell of claim 4 in a medium under conditions permitting expression of a polypeptide encoded by the nucleic acid, and purifying the polypeptide from the cultured cell or the medium of the cell.

* * * * *